United States Patent
Takeya et al.

(10) Patent No.: US 9,853,225 B2
(45) Date of Patent: Dec. 26, 2017

(54) CHALCOGEN-CONTAINING ORGANIC COMPOUND AND A USE THEREOF

(71) Applicants: JNC CORPORATION, Tokyo (JP); PI-CRYSTAL INCORPORATION, Osaka (JP)

(72) Inventors: Junichi Takeya, Chiba (JP); Toshihiro Okamoto, Chiba (JP); Chikahiko Mitsui, Chiba (JP); Takeshi Matsushita, Chiba (JP)

(73) Assignees: JNC CORPORATION, Tokyo (JP); PI-CRYSTAL INCORPORATION, Osaka (JP)

(*) Notice: Subject to any disclaimer, the term of this patent is extended or adjusted under 35 U.S.C. 154(b) by 0 days.

(21) Appl. No.: 14/772,095

(22) PCT Filed: Mar. 5, 2014

(86) PCT No.: PCT/JP2014/055597
§ 371 (c)(1),
(2) Date: Sep. 2, 2015

(87) PCT Pub. No.: WO2014/136827
PCT Pub. Date: Sep. 12, 2014

(65) Prior Publication Data
US 2016/0013425 A1 Jan. 14, 2016

(30) Foreign Application Priority Data
Mar. 5, 2013 (JP) .................. 2013-042762

(51) Int. Cl.
| H01L 51/00 | (2006.01) |
| H01L 51/05 | (2006.01) |
| C07D 517/04 | (2006.01) |
| C07D 493/04 | (2006.01) |
| C07D 495/04 | (2006.01) |

(52) U.S. Cl.
CPC ........ *H01L 51/0073* (2013.01); *C07D 493/04* (2013.01); *C07D 495/04* (2013.01); *C07D 517/04* (2013.01); *H01L 51/0071* (2013.01); *H01L 51/0074* (2013.01); *H01L 51/0558* (2013.01)

(58) Field of Classification Search
CPC ............. H01L 51/0073; H01L 51/0071; H01L 51/0074; H01L 51/0558; C07D 517/04; C07D 493/04; C07D 495/04
See application file for complete search history.

(56) References Cited

U.S. PATENT DOCUMENTS

| 2008/0061287 A1 | 3/2008 | Nagata et al. |
| 2009/0001357 A1 | 1/2009 | Takimiya et al. |
| 2009/0261300 A1 | 10/2009 | Watanabe |
| 2009/0299070 A1 | 12/2009 | Berens et al. |
| 2010/0065826 A1 | 3/2010 | Takimiya et al. |
| 2011/0024731 A1 | 2/2011 | Takimiya et al. |
| 2015/0166560 A1* | 6/2015 | Kitamura ............ H01L 51/0073 257/40 |

FOREIGN PATENT DOCUMENTS

| JP | 2009-203183 | 9/2009 |
| JP | 2010-138077 | 6/2010 |
| JP | 2014-45099 | 3/2014 |
| WO | 2005/080304 | 9/2005 |
| WO | 2006/077888 | 7/2006 |
| WO | 2007/068618 | 6/2007 |
| WO | 2008/026602 | 3/2008 |
| WO | 2008/050726 | 5/2008 |
| WO | 2010-87408 | 4/2010 |

(Continued)

OTHER PUBLICATIONS

WO 2014034393 A1 ProQuest English Machine Translation Dec. 1, 2016; p. 1-35.*

(Continued)

*Primary Examiner* — Matt Mauro
(74) *Attorney, Agent, or Firm* — Wenderoth, Lind & Ponack, L.L.P.

(57) ABSTRACT

A compound is represented by Formula (1):

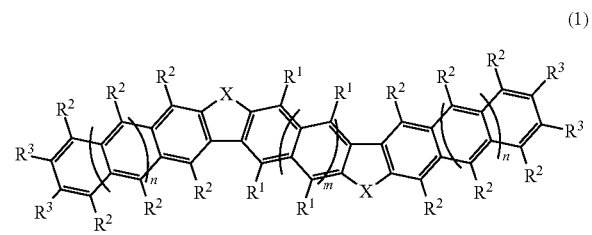

wherein, each X is independently oxygen, sulfur, or selenium; m is 0 or 1; each n is independently 0 or 1; $R^1$-$R^3$ are each independently, for example, hydrogen or alkyl having 1 to 20 carbons;

wherein (i) in the case of m=0, it is excluded that all of $R^1$-$R^3$ are hydrogen at the same time;

(ii) in the case of m=0, n=0 and in the case that m is 0, one of n is 0 and the other is 1, it is excluded that "both of X are sulfur and all $R^3$s are the same atoms or groups at the same time";

(iii) in the case of m=0, n=1, it is excluded that all $R^3$s are the same atoms or groups at the same time, and at least one of $R^3$s is hydrogen.

9 Claims, 5 Drawing Sheets

(56) References Cited

FOREIGN PATENT DOCUMENTS

| WO | 2010/098372 | 9/2010 |
|---|---|---|
| WO | 2011/074231 | 6/2011 |
| WO | 2014/034393 | 3/2014 |

OTHER PUBLICATIONS

WO 2014034393 A1 WIPO English Machine Translation Dec. 1, 2016; p. 1-17.*
WO 2008026602 A1 ProQuest English Machine Translation Dec. 1, 2016; p. 1-69.*
JP 2009203183 A ProQuest English Machine Translation; Dec. 1, 2016; p. 1-54.*
Ebata et al., Highly Soluble [1]Benzothieno[3,2-b]benzothlophene (BTBT) Derivatives for High-Performance, Solution-Processed Organic Field-Effect Transistors, Journal of the American Chemical Society, vol. 129, No. 51, 2007, pp. 15732-15733.
Supplementary Partial European Search Report dated Jul. 5, 2016 in corresponding European Patent Application No. 14760923.4.
First Office Action dated Aug. 1, 2016 in Chinese Application No. 201480012257.7, with English translation.
Yong-Hwan Cho et al., "Asymmetric Synthesis of Axially Chiral Biaryls by Nickel-Catalyzed Grignard Cross-Coupling of Dibenzothiophenes", J. Org. Chem., vol. 69, No. 11, 2004, pp. 3811-3823.
Attilio Arienti et al., "Highly selective conversion of hydroxylated biaryls to dibenzofuran derivatives over zeolite catalyst", J. Chem. Soc., Perkin Trans. 1, pp. 1391-1393.
International Search Report dated Apr. 15, 2014 in International Application No. PCT/JP2014/055597.
John E. Anthony et al., "Functionalized Pentacene: Improved Electronic Properties from Control of Solid-State Order" Journal of the American Chemical Society, 2001, 123, pp. 9482-9483.
Masakazu Yamagishi et al., "High Performance-OFETs of New V-shape Fused in II-Conjugated Semiconductors", 59th Meeting of the Japan Society of Applied Physics and Related Societies, Lecture No. 16aF9-7, (2012).
Cui-Hua Wang et al., "Linear $C_2$-symmetric polycyclic benzodithiophene: efficient, highly diversified approaches and the optical properties", Tetrahedron Letters 46, 2005, 8153-8157.

* cited by examiner

[Fig. 1]
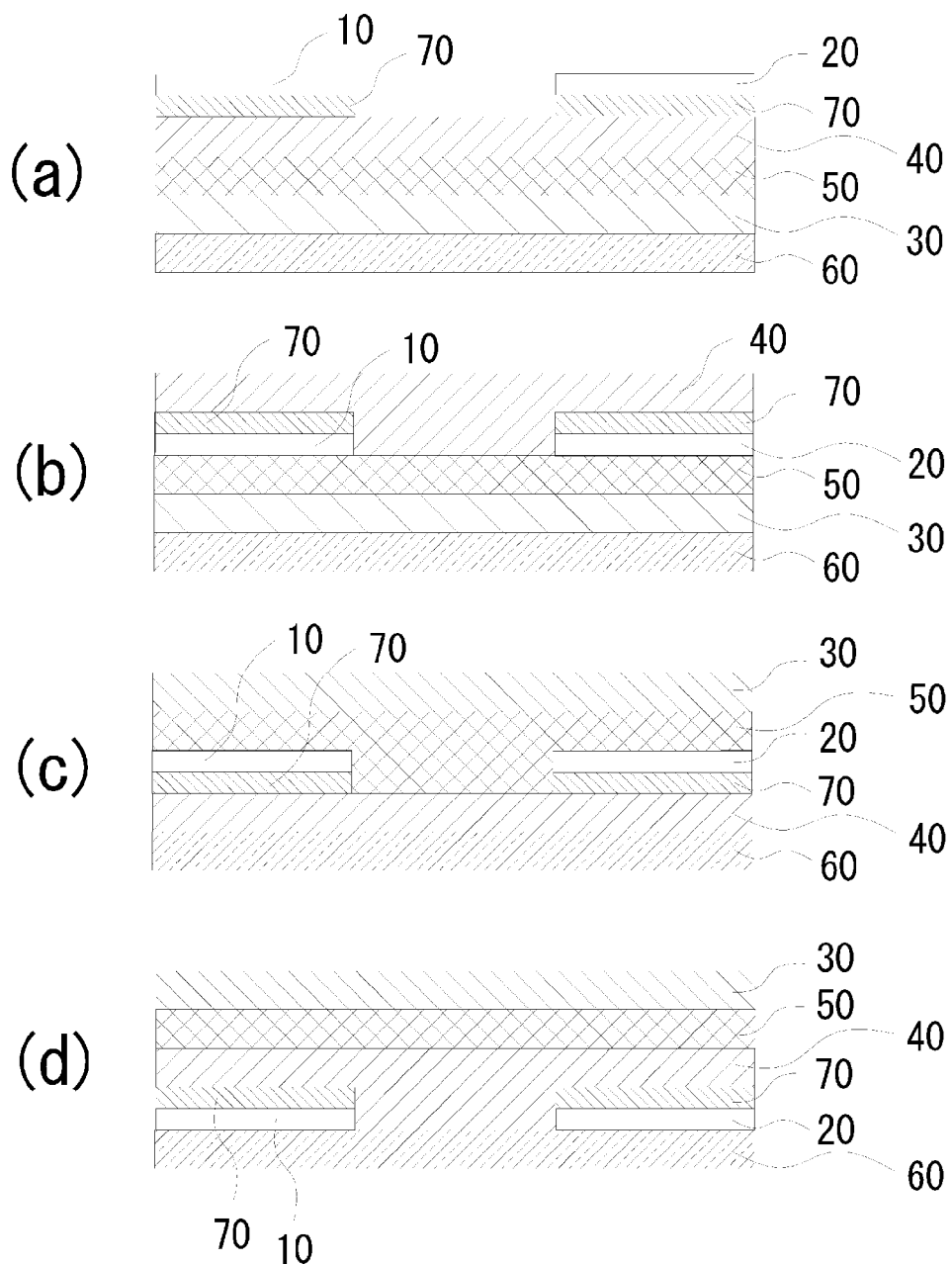

[Fig. 2]
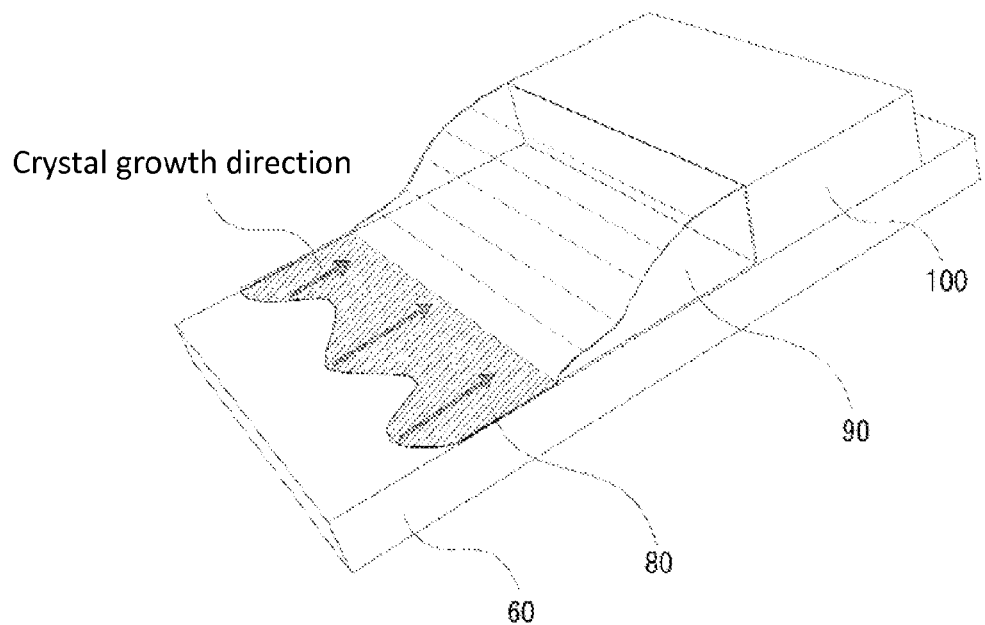
[Fig. 3]
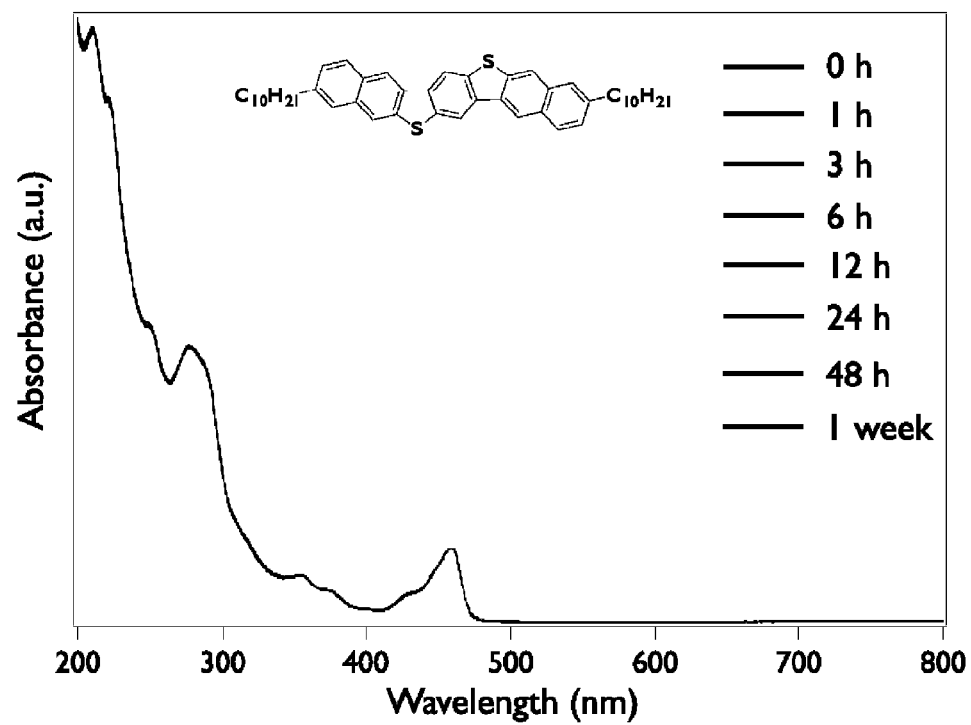

[Fig. 4]
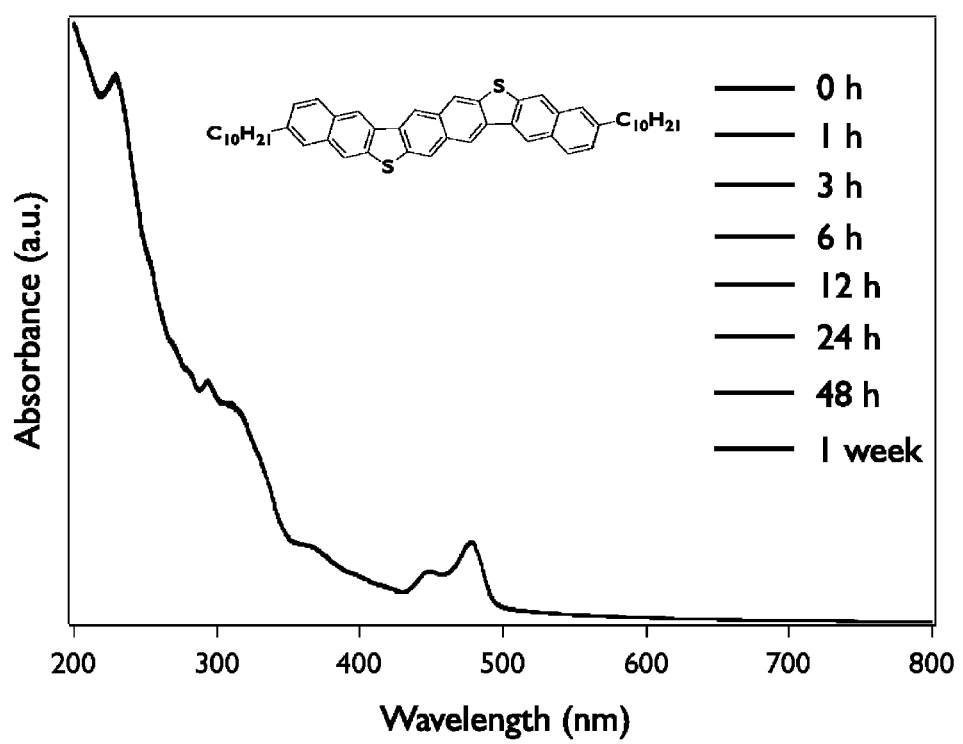

[Fig. 5]
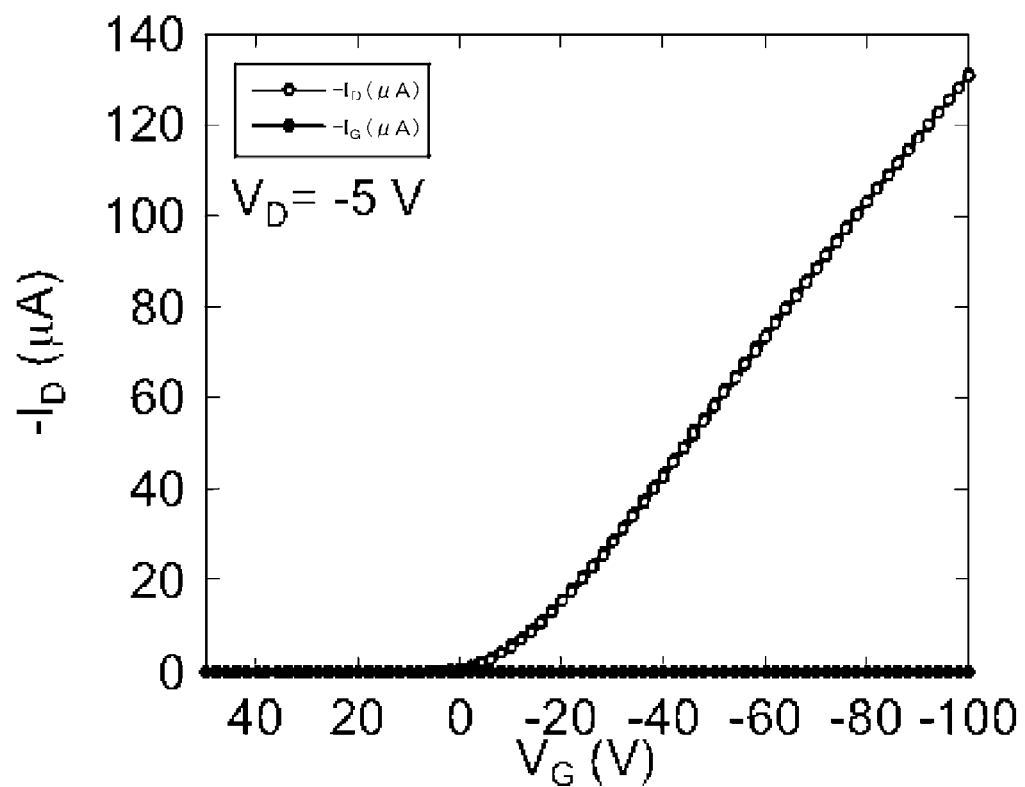

[Fig. 6]
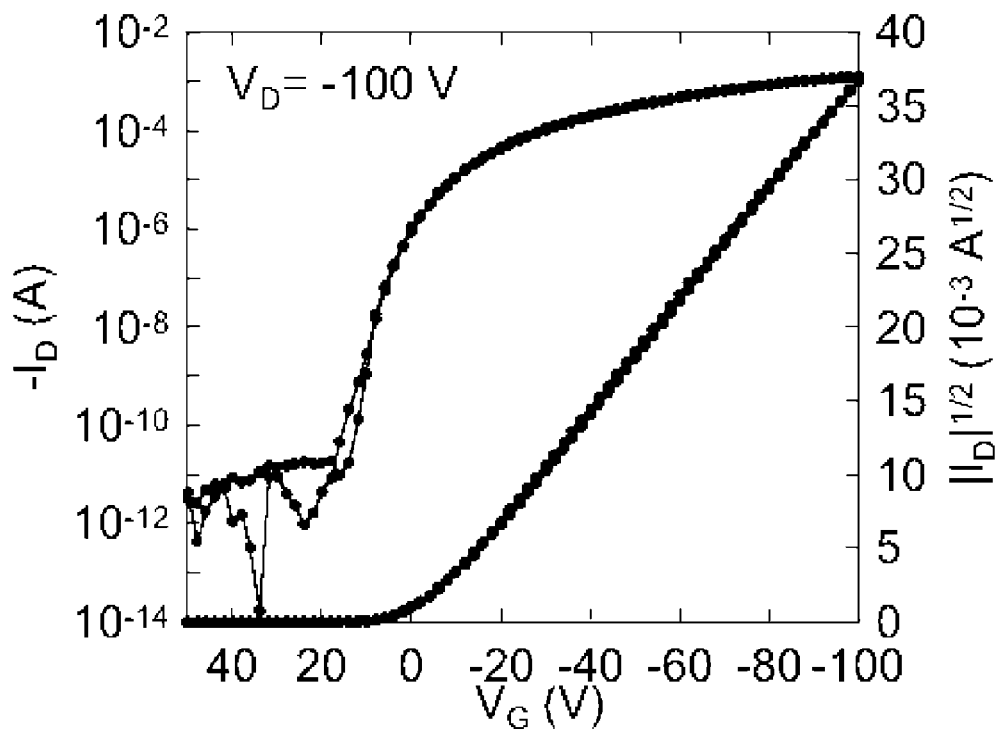
[Fig. 7]
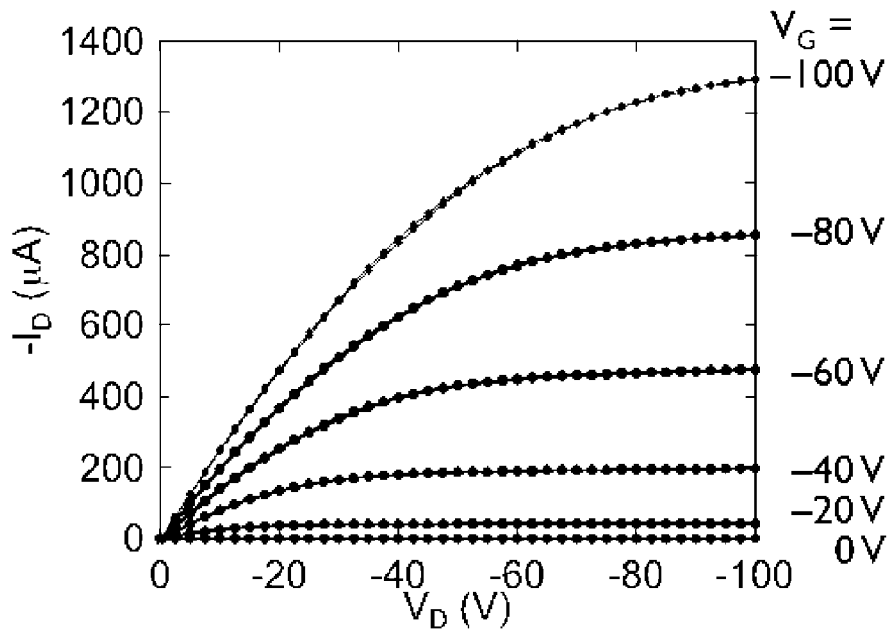

CHALCOGEN-CONTAINING ORGANIC COMPOUND AND A USE THEREOF

TECHNICAL FIELD

The present invention relates to a chalcogen-containing organic compound and a use thereof. More specifically, the invention relates to a chalcogen-containing organic compound and a method for manufacturing the same, an organic semiconductor material composed of the organic compound, an organic semiconductor film including the organic semiconductor material and an organic field effect transistor (FET) having the organic semiconductor film.

BACKGROUND ART

In recent years, organic compounds having semiconducting properties have attracted attention. Among the organic compounds, a polyacene compound such as pentacene and tetracene has been known as an organic semiconductor material due to high carrier mobility thereof for many years. "Carrier mobility" herein is used in a broad sense, including electron mobility and hole mobility.

However, publicly known polyacene compounds have low solubility in a solvent, and therefore it is difficult to form films by an application method, a printing method or the like. Therefore, there is no choice other than a vapor deposition method requiring high manufacturing cost for preparing a device having semiconductor characteristics (hereinafter, also referred to as "device"). Further, the publicly known polyacene compounds also have a problem on chemical stability such as oxidation resistance, and therefore these are difficult materials from a viewpoint of industrial practicality.

Consequently, studies have been carried out on compounds in which various substituents are introduced on an acene skeleton (see Patent literature No. 1 and Non-patent literature No. 1, for example) in order to improve the solubility and the chemical stability. Further, also studies have been already carried out on compounds in which chalcogen such as sulfur and selenium is introduced on a part of an acene skeleton, for example, dibenzothienothiophene (BTBT) and dinaphthothienothiophene (DNTT) (see Patent literature Nos. 2 to 3, for example).

According to the Patent literatures, success has been made in improving the chemical stability in the compounds while high carrier mobility is maintained. However, those compounds have linear and highly symmetrical molecular structure, and therefore have a problem of solubility being not necessarily sufficient even if a substituent such as an alkyl group is introduced thereon, or the like. Moreover, as the molecular structure becomes further complicated, the compounds can be barely synthesized using an expensive raw material or a reactant having a high environmental load, and through multi-step synthesis.

Thus, various kinds of organic compounds having semiconductor characteristics have been developed so far. However, development has not sufficiently been made yet for an organic compound that is easily synthesized, and that has excellent thermal•chemical stability, high solubility in a solvent and high carrier mobility (material that can be applied or printed in a solution state, and can be applied to a wide range of uses, such as transistor preparation).

Therefore, an organic semiconductor material having a nonlinear type structure as a basic skeleton that has a bending part in the molecule have attracted attention in recent years. In regard to the above mentioned organic semiconductor material, the present inventors have already introduced a substituent(s) such as an alkyl group at a specific position(s) on the V- or U-shaped molecule such as dinaphthofuran, dinaphthothiophene, dianthrafuran and dianthrathiophene or the like, and then come to find organic semiconductor materials being excellent at thermal•chemical stability, also having high solubility and high carrier mobility (see non-patent literature No. 2).

As the further research of the above mentioned organic semiconductor material, the present inventors have given attention to kinds of N-shaped molecule having two bending parts in the molecule itself; these are dibenzodichalcogenoacenes, dinaphtodichalcogenoacenes and dianthradichalcogenoacenes.

Also of these N-shaped molecules, several examples have been already disclosed (see Patent literatures Nos. 4-8).

In Patent literatures No. 4-6, there are mentioned regarding dibenzodichalcogenoacene, dinaphtodichalcogenoacene and dianthradichalcogenoacene, and also derivatives of these, organic semiconductor materials and organic films including these compounds, and also their usage.

However in Patent literature No. 4, nothing is proofed about the semiconducting property of the compounds, and also nothing can be found about the effect that comes from introduction of the substituents. In addition, regarding derivatives of the compounds on which one to three alkyl groups or phenyl groups are introduced, the compounds themselves are not disclosed, and also nothing is found about solubility of the compounds to solvents, applicability of solutions including the compounds, nor semiconducting property of the compounds.

Further in Patent literatures 5-6, dinaphtodichalcogenoacen and its derivative are not disclosed, nothing is proofed about the semiconducting property of dibenzodichalcogenoacene and dianthradichalcogenoacene, and also of derivatives of these, and nothing can be found about the effect that comes from introduction of the substituents. In addition, regarding a derivative of dianthradichalcogenoacene on which one to three alkyl groups or phenyl groups are introduced, the compound itself is not disclosed, and also nothing is found about solubility of the compound to solvents, applicability of solutions including the compound, nor semiconducting property of the compound.

Furthermore, in Patent literatures Nos. 7-8, dibenzodicarcogenoacene derivative is disclosed as represented by almost the same formula below, but nothing is disclosed about dinaphtodichalcogenoacen and dianthradichalcogenoacene, and also their derivateves.

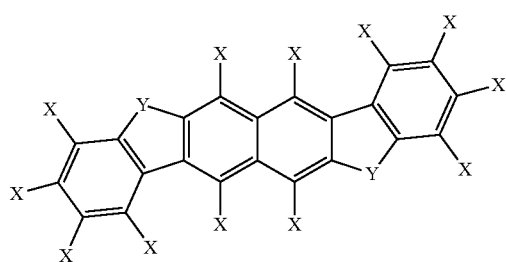

In the formula, Y is oxygen or sulfur etc., and X is a substituent of various kinds.

Also as an organic semiconductor material, a benzodithiophene of multi-ring type represented by the following formula is disclosed (see Non-Patent literature No. 3). However, nothing can be found about semiconducting property of the compound, and no proof for its usability as an organic semiconductor material is disclosed.

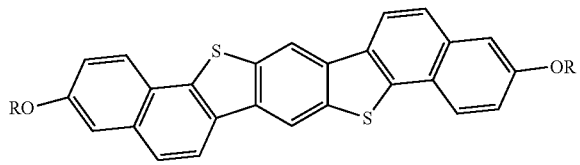

In the formula, R is —$C_6H_{13}$ or -TIPS (triisopropylsilyl).

CITATION LIST

Patent Literature

[Patent literature 1] WO 2005/80304 A
[Patent literature 2] WO 2006/77888 A
[Patent literature 3] WO 2008/50726 A
[Patent literature 4] WO 2008/26602 A
[Patent literature 5] JP 2009-203183 A
[Patent literature 6] JP 2010-138077 A
[Patent literature 7] JP 2010-87408 A
[Patent literature 8] WO 2011/74231 A Non-Patent Literature

[Non-Patent literature 1] Journal of the American Chemical Society, No. 123, P. 9482, 2001
[Non-Patent literature 2] 59th Meeting of The Japan Society of Applied Physics and Related Societies, Lecture No. 16aF9-7, (2012)
[Non-Patent literature 3] Tetrahedron Letters 46, 2005, 8153-8157

SUMMARY OF INVENTION

Technical Problem

There is high availability of an organic compound being easily synthesized, being excellent at thermal•chemical stability, having semiconductor property (high carrier mobility), and having high solubility in a solvent, since it makes the film formation possible with the application method or the printing method etc., by using a solution including the compound.

Accordingly, an object of the present invention is to provide an organic compound being easily synthesized, being excellent at thermal•chemical stability, having semiconductor property (high carrier mobility), and having high solubility in a solvent; a method for producing the organic compound, an organic semiconductor material composed of the organic compound; an organic semiconductor film including the organic semiconductor material; and also an organic field effect transistor (FET) having the organic semiconductor film.

Solution to Problem

The present inventors have made a researching work in order to solve the problem. As a result, the present inventors have found the solution by the following chalcogen-containing organic compound having N-shaped molecular structure, and have come to complete the present invention.

That is, the present invention relates to the following [1] to [12].

[1] A compound represented by Formula (1).

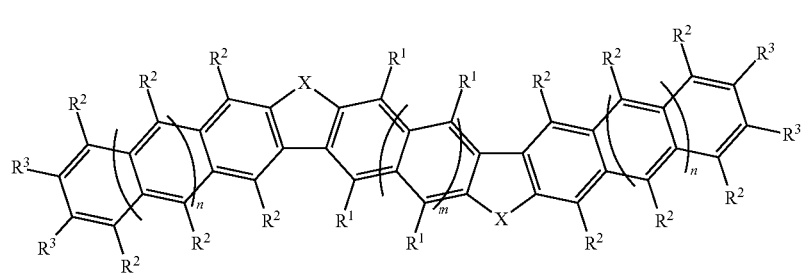

(1)

wherein, in Formula (1), each X is independently oxygen, sulfur, or selenium; m is 0 or 1; each n existing at two positions is independently 0 or 1; $R^1$-$R^3$ are each independently hydrogen, fluorine, alkyl having 1 to 20 carbons, aryl, pyridyl, furyl, thienyl or thiazolyl, at least one hydrogen in the alkyl may be replaced with fluorine, and at least one hydrogen on a ring of the aryl, pyridyl, furyl, thienyl and thiazolyl may be replaced with at least one kind selected from fluorine and alkyl having 1 to 10 carbons;

wherein (i) in the case of m=0, it is excluded that all of $R^1$-$R^3$ are hydrogen at the same time;

(ii) in the case that m is 0 and both of n are 0, and in the case that m is 0, one of n is 0 and the other is 1, it is excluded that "both of X are sulfur and all $R^3$s are the same atoms or groups at the same time";

(iii) in the case that m is 0 and both of n are 1, it is excluded that all $R^3$s are the same atoms or groups at the same time, and at least one of $R^3$s is hydrogen.

[2] The compound described in the above [1], wherein all of $R^1$-$R^2$ in Formula (1) are hydrogen at the same time.

[3] The compound described in the above [1] or [2], wherein the case that the all $R^3$s in Formula (1) are the same atoms or groups is excluded.

[4] The compound described in any one of the above [1]-[3], wherein at least one of $R^3$s in Formula (1) is hydrogen.

[5] The compound described in the above [4], which is represented by Formula (1-1) or Formula (1-2).

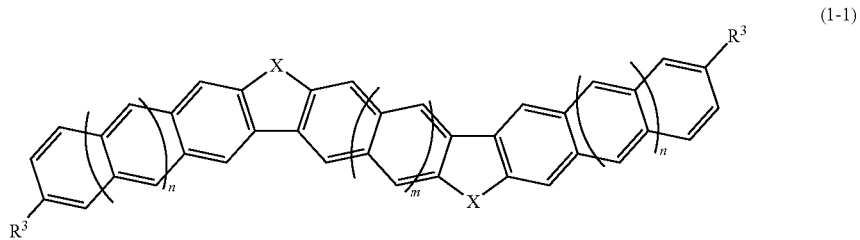

(1-1)

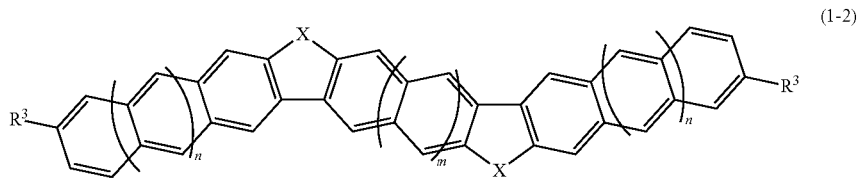

(1-2)

wherein, in Formula (1-1) and Formula (1-2), the definitions of X, m and n are the same as the corresponding symbols of those in Formula (1) respectively; each $R^3$ existing at two positions is independently fluorine, alkyl having 1 to 20 carbons, aryl, pyridyl, furyl, thienyl or thiazolyl, at least one hydrogen in the alkyl may be replaced with fluorine, and at least one hydrogen on a ring of the aryl, pyridyl, furyl, thienyl and thiazolyl may be replaced with at least one kind selected from fluorine and alkyl having 1 to 10 carbons.

[6] The compound described in the above [5], wherein $R^3$s in Formula (1-1) and Formula (1-2) are the same group selected from alkyl having 1 to 20 carbons, phenyl, furyl and thienyl.

[7] The compound described in the above [6], wherein $R^3$s in Formula (1-1) and Formula (1-2) are the same group selected from alkyl having 9 to 12 carbons.

[8] A method for producing the compound described in the above [1] with the proviso that X is sulfur or selenium, comprising a step of cross-coupling a compound represented by Formula (11) and a compound represented by Formula (12) to obtain a compound represented by Formula (13); a step of deprotecting the methoxy from the compound represented by Formula (13) to obtain a compound represented by Formula (14); a step of allowing the compound represented by Formula (14) to react with N,N-dialkyl carbamoylthiochloride or N,N-dialkyl carbamoylselenochloride to obtain a compound represented by formula (15); and a step of heating the compound represented by Formula (15) to obtain the compound represented by Formula (1),

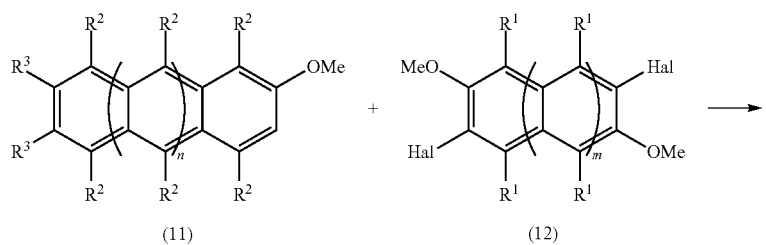

(11)    (12)

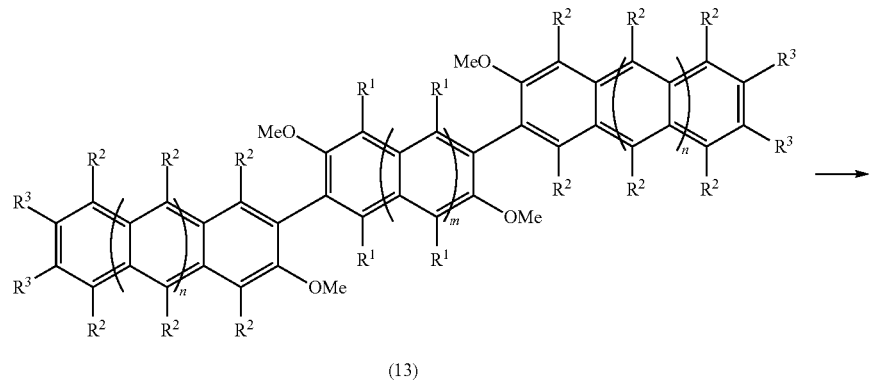

(13)

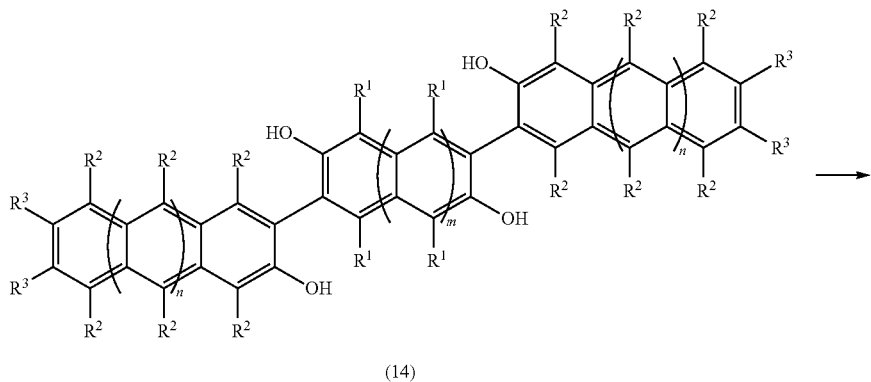

(14)

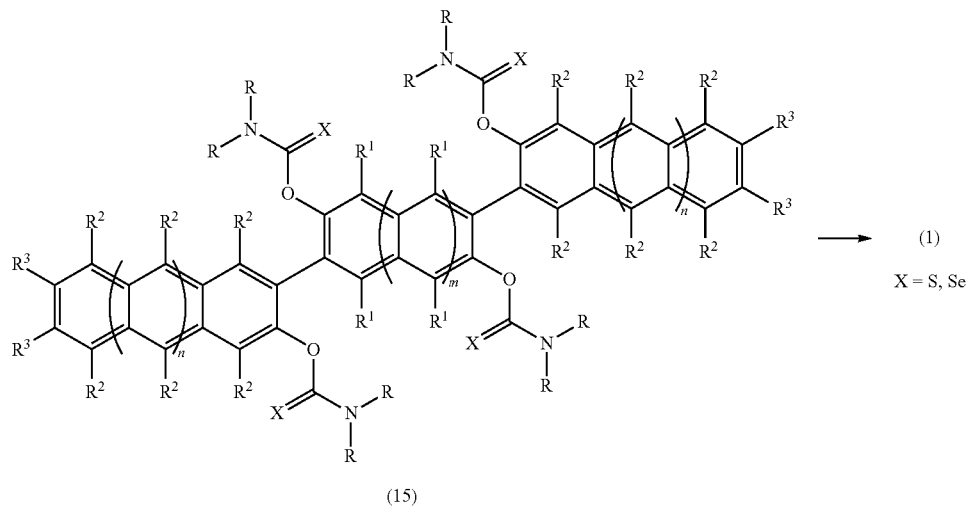

(15)

X = S, Se wherein, in Formulae (11)-(15), the definitions of m, n and $R^1$-$R^3$ are the same as the corresponding symbols of those in Formula (1) respectively, Me is methyl, Hal is bromine or iodine, and each R is independently alkyl having 1-3 carbons.

[9] A method for producing the compound described in the above [1] with the proviso that X is oxygen, comprising a step of cross-coupling a compound represented by Formula (11) and a compound represented by Formula (12) to obtain a compound represented by Formula (13); a step of deprotecting the methoxy from the compound represented by Formula (13) to obtain a compound represented by Formula (14); and a step of heating and dehydrating the compound represented by Formula (14) under a zeolite catalyst to obtain the compound represented by Formula (1),

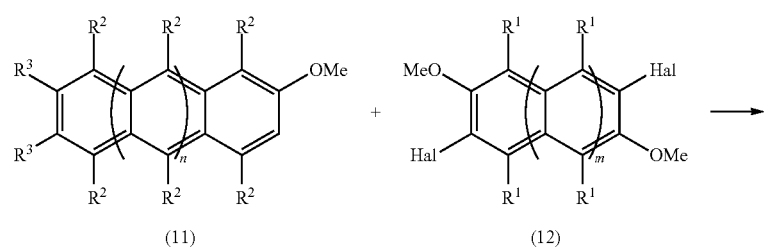

(11)  (12)

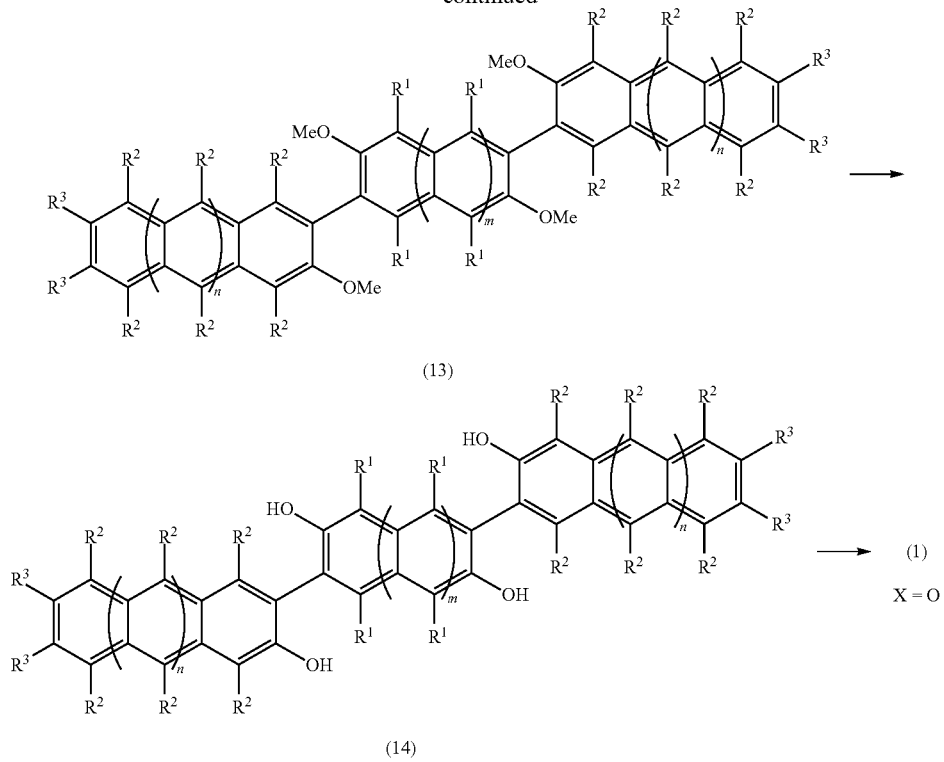

(13)

(14)

wherein, in Formulae (11)-(14), the definitions of m, n and $R^1$-$R^3$ are the same as the corresponding symbols of those in Formula (1) respectively, Me is methyl, and Hal is bromine or iodine.

[10] An organic semiconductor material comprising the compound described in any one of the above [1]-[7].

[11] An organic semiconductor film comprising the organic semiconductor material described in the above [10].

[12] An organic field effect transistor comprising a substrate, a gate electrode, a gate insulating film, a source electrode, a drain electrode and an organic semiconductor layer, wherein the organic semiconductor layer is constituted of the organic semiconductor film described in the above [11].

Advantageous Effects of Invention

The present invention can provide an organic compound being easily synthesized, being excellent at thermal•chemical stability, having semiconductor property (high carrier mobility), and having high solubility in a solvent; a method for producing the organic compound; an organic semiconductor material composed of the organic compound; an organic semiconductor film including the organic semiconductor material; and also an organic field effect transistor (FET) having the organic semiconductor film.

BRIEF DESCRIPTION OF DRAWINGS

FIG. 1 is a cross-sectional view of an organic field effect transistor (FET) having a bottom gate-top contact type (a), a bottom gate-bottom contact type (b), a top gate-top contact type (c) or a top gate-bottom contact type (d).

FIG. 2 shows an outline of film formation by edge-cast method.

FIG. 3 shows a UV-VIS absorption spectrum of a synthesized compound (a solution).

FIG. 4 shows a UV-VIS absorption spectrum of the synthesized compound (a film).

FIG. 5 shows transfer characteristics of the compound in linier zone, wherein the compound is formed as a film by edge-cast method.

FIG. 6 shows transfer characteristics of the compound in saturating zone, wherein the compound is formed as a film by edge-cast method.

FIG. 7 shows output characteristics of the compound being formed as a film by edge-cast method.

DESCRIPTION OF EMBODIMENTS

The present invention will be explained in detail as follows.

[Chalcogen-Containing Organic Compound]

A chalcogen-containing organic compound of the present invention is a compound represented by Formula (1), and has a N-shaped molecular structure (Formula (1)) in which benzene rings are connected at bridging parts of chalcogen (—X—) as bending points toward the both side wings, and preferably has a substituent at an arbitrary position on the benzene rings. In the present description, "substituent" means an atom or group other than hydrogen.

The compound represented by Formula (1) is also referred to as "Compound (1)", alternatively referred to as "the compound of the present invention". Further, the compounds represented by other Formulae (i) are also referred to as "Compound (i)" (i represents Formula number).

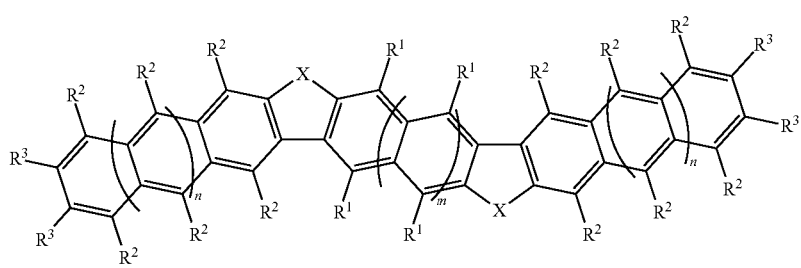

(1)

In Formula (1), the meaning of each symbol is as follows:

Each X is independently oxygen, sulfur or selenium, and as the compound of the present invention shall show high carrier mobility, X is preferably oxygen or sulfur, and especially sulfur is preferred.

m is 0 or 1, and preferably 0.

Each n existing at two positions is independently 0 or 1, and preferably 0 from a view point of solubility.

$R^1$, $R^2$ and $R^3$ are each independently hydrogen, fluorine, alkyl having 1 to 20 carbons, aryl, pyridyl, furyl (furan ring), thienyl (thiophene ring) or thiazolyl (thiazole ring). At least one hydrogen in the alkyl may be replaced with fluorine. At least one hydrogen on a ring of the aryl, pyridyl, furyl, thienyl and thiazolyl may be replaced with at least one kind selected from fluorine and alkyl having 1 to 10 (preferably 1 to 6, more preferably 1 to 3) carbons.

"Each independently" in the definitions of $R^1$, $R^2$ and $R^3$ means not only the case where $R^1$, $R^2$ and $R^3$ may be the same or different with each other, but also means the cases where $R^1$s existing at plural positions may be the same or different with each other, where $R^2$s existing at plural positions may be the same or different with each other, and where $R^3$s existing at plural positions may be the same or different with each other.

In Formula (1), in the case where both of m, n are 0, it is preferred that the atoms or the groups bonded with carbon atoms at the 2nd and the 10th positions are the same, and also similarly preferred that the atoms or the groups bonded with carbon atoms respectively at the 3rd and the 11th positions, at the 1st and the 9th positions, at the 4th and the 12th positions, at the 5th and the 13th positions, at the 7th and the 15th positions, at the 8th and the 16th positions are the same.

In Formula (1), in the case where m is 0 and both of n are 1, it is preferred that the atoms or the groups bonded with carbon atoms at the 2nd and the 12th positions are the same, and also similarly preferred that the atoms or the groups bonded with carbon atoms respectively at the 3rd and the 13th positions, at the 1st and the 11th positions, at the 4th and the 14th positions, at the 5th and the 15th positions, at the 6th and the 16th positions, at the 8th and the 18th positions, at the 9th and the 19th positions, at the 10th and the 20th positions are the same.

In Formula (1), in the case where m is 1 and both of n are 0, it is preferred that the atoms or the groups bonded with carbon atoms at the 2nd and the 11th positions are the same, and also similarly preferred that the atoms or the groups bonded with carbon atoms respectively at the 3rd and the 12th positions, at the 1st and the 10th positions, at the 4th and the 13th positions, at the 5th and the 14th positions, at the 7th and the 16th positions, at the 8th and the 17th positions, at the 9th and the 18th positions are the same.

In Formula (1), in the case where all of m and n are 1, it is preferred that the atoms or the groups bonded with carbon atoms at the 2nd and the 13th positions are the same, and also similarly preferred that the atoms or the groups bonded with carbon atoms respectively at the 3rd and the 14th positions, at the 1st and the 12th positions, at the 4th and the 15th positions, at the 5th and the 16th positions, at the 6th and the 17th positions, at the 8th and the 19th positions, at the 9th and the 20th positions, at the 10th and the 21st positions, at the 11th and the 22nd positions are the same.

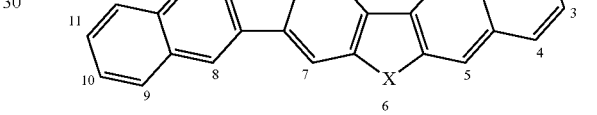

m = n = 0

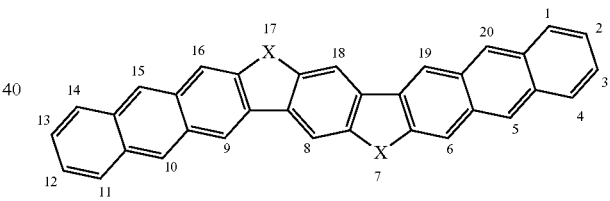

m = 0, n = 1

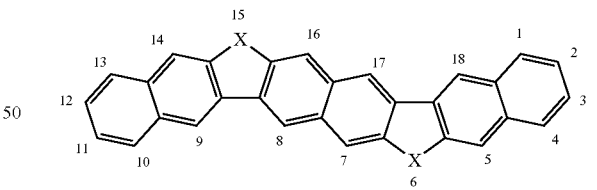

m = 1, n = 0

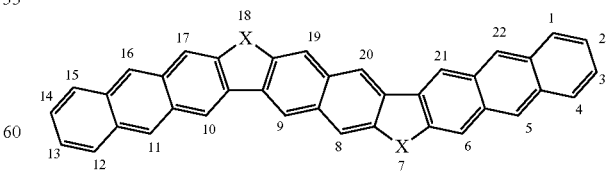

m = n = 1

However, a provision is given in Formula (1), (i) under the case that m=0, it is excluded that all of $R^1$ to $R^3$ are hydrogen at the same time. Also under the case that m=1, it is preferably excluded that all of $R^1$ to $R^3$ are hydrogen at the same time.

As an additional provision in Formula (1), (ii) when both of n are 0 under the case that m is 0; and when one of n is 0 and the other is 1 under the case that m is 0; it is excluded that "both of X are sulfur and all $R^3$s are the same atoms or groups at the same time". It means that in the case that m is 0 and both of n are 0; and in the case that m is 0, one of n is 1 and the other is 0; it is excluded that "both of X are sulfur and all $R^3$s are the same atoms or groups at the same time".

As a further additional provision in Formula (1), (iii) when both of n are 1 under the case that m is 0; it is excluded that all $R^3$s are the same atoms or groups at the same time; and at least one of $R^3$s is hydrogen.

In Formula (1), it is preferred that all of $R^1$-$R^2$ are hydrogen at the same time. Also it is preferred that a case that all (four) $R^3$s are the same atoms or groups at the same time is excluded. Further it is preferred that at least one of (four) $R^3$s is hydrogen.

Examples of the alkyl having 1 to 20 carbons listed for $R^1$-$R^3$ in Formula (1) include methyl, ethyl, propyl, butyl, pentyl, hexyl, heptyl, octyl, nonyl, decyl, dodecyl, undecyl and octadecyl. The carbon number of the alkyl is preferably 4 to 15, more preferably 6 to 12, and especially preferably 9 to 12, from a viewpoint that the compound of the present invention compatibly could have high solubility in a solvent and intermolecular overlapability of electron clouds. The alkyl can be any of a straight chain and a branched chain, and preferably it is a straight chain from a viewpoint of molecular alignment in crystal.

Examples of the group in which at least one hydrogen in the alkyl is replaced with fluorine include a group in which all hydrogens in the alkyl are replaced with fluorine, such as, trifluoromethyl, perfluorohexyl, perfluorooctyl and perfluorodecyl; and a group in which only hydrogen bonded with a carbon directly bonded with an aromatic ring is not replaced with fluorine, and all other hydrogens are replaced with fluorine, such as, trifluoroethyl, 1H,1H-perfluorohexyl, 1H,1H-perfluorooctyl and 1H,1H-perfluorodecyl.

Examples of the aryl listed for $R^1$-$R^3$ in Formula (1) include phenyl, naphthyl, (example: 1-naphthyl, 2-naphthyl), fluorenyl (example: 2-fluorenyl) and biphenyl. The carbon number of the aryl is preferably 6 to 14, and more preferably 6 to 10. Among these, phenyl is especially preferred.

Examples of the pyridyl listed for $R^1$-$R^3$ in Formula (1) include 2-pyridyl, 3-pyridyl and 4-pyridyl.

1e;2qExamples of the group in which at least one hydrogen on a ring of the aryl is replaced with an alkyl having 1 to 10 carbons include tolyl and xylyl. Examples of the group in which at least one hydrogen on a ring of the aryl is replaced with fluorine include p-fluorophenyl, pentafluorophenyl.

Examples of the furyl listed for $R^1$-$R^3$ in Formula (1) include 2-furyl, 3-furyl; as the thienyl, for example, it can be 2-thienyl and 3-thienyl; as the thiazolyl, for example, it can be 2-thiazolyl.

Among the compounds (1) of the present invention, from a viewpoint of assembling the organic semiconductor molecules with high density, a derivative having two substituents, that is, a compound represented by Formula (1-1) or Formula (1-2) is preferred, and from a viewpoint that it shows high carrier mobility, the compound represented by Formula (1-2) is especially preferred.

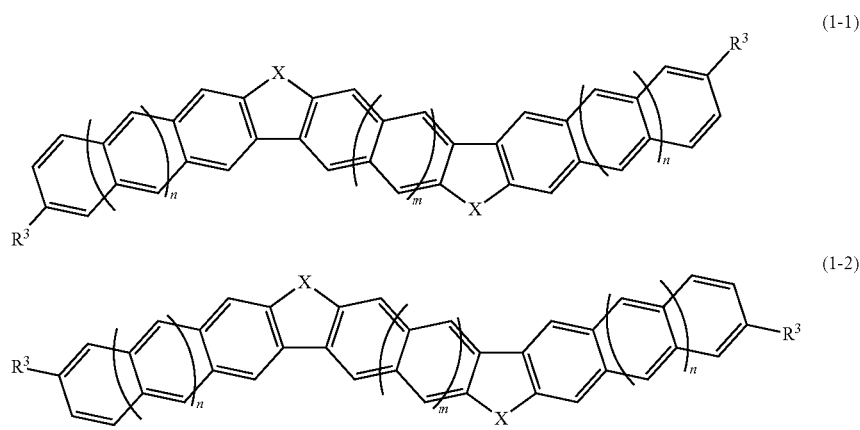

In Formula (1-1) and Formula (1-2), the definitions of X, m and n are the same as the corresponding symbols of those in Formula (1) respectively. Each $R^3$ existing at two positions is independently fluorine, alkyl having 1 to 20 carbons, aryl, pyridyl, furyl, thienyl or thiazolyl. At least one hydrogen in the alkyl may be replaced with fluorine. At least one hydrogen on a ring of the aryl, pyridyl, furyl, thienyl and thiazolyl may be replaced with at least one kind selected from fluorine and alkyl having 1 to 10 carbons. The embodiments and preferred examples for these substituents are mentioned in the explanation of Formula (1).

In Formula (1-1) and Formula (1-2), $R^3$s existing at two positions can be the same or different with each other, and are preferably the same substituent. $R^3$s existing at two positions are preferably the same group selected from alkyl having 1 to 20 carbons, phenyl, furyl and thienyl, more preferably alkyls having 1 to 20 carbons, and with the reason that the compound of the present invention shows high carrier mobility, further more preferred are alkyls having 4 to 15 carbons, especially preferred are alkyls having 6 to 12 carbons, and the most preferred are alkyls having 9 to 12 carbons.

Formula (1-1), Formula (1-2) are, for example, the following formulae.

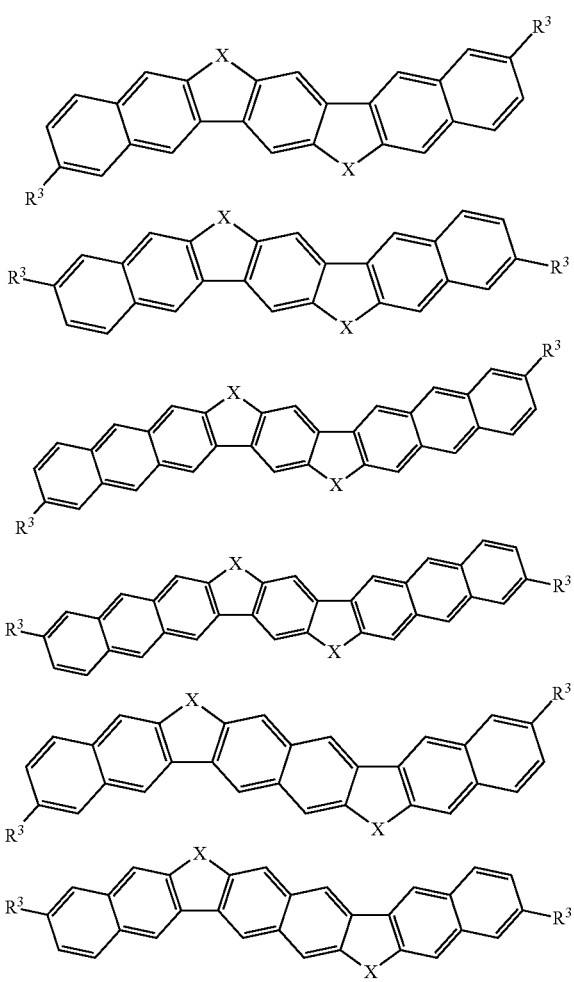

The compound of the present invention shows high solubility in a solvent, since it gets being effected by its structure (non-linear and chalcogen bridging structure) and preferably by introducing substituent(s), compared with linear molecules having similar number of rings. It means that, with the compound's concentration explained later, a solution can be prepared. Therefore, it become possible to apply or print the solution including the compound of the present invention on a substrate, and with a simple film formation method, the organic semiconductor film including the compound of the present invention can be produced. For example, as a film formation using the printing method can be carried out under normal temperature and ordinary pressure, and also as it can form the film easily within short time, it is more advantageous than a vapor deposition method or the like being carried out under high temperature and high pressure, in viewpoints of manufacturing cost etc. Therefore the organic semiconductor film and the device having the organic semiconductor film can be produced, without spoiling excellence of the compound of the present invention.

In the compound of the present invention, intermolecular interaction is improved by the chalcogen existing at the bending part of the molecule, and it holds enough intermolecular overlapping of π electron orbits. Therefore, the compound of the present invention and the organic semiconductor film including this compound show sufficiently high carrier mobility. Although an optimum value of the carrier mobility could be varied depending on the usage, in the case of the usage for the organic semiconductor device, preferred carrier mobility is not less than 0.01 cm$^2$/V·s, more preferred is not less than 5.0 cm$^2$/V·s, and especially preferred is not less than 10.0 cm$^2$/V·s. The maximum value of the carrier mobility is not specified, but for example, it is approximately 50.0 cm$^2$/V·s. The carrier mobility can be measured, for example, as on an organic semiconductor film formed using a solution of the compound of the present invention at a concentration of 0.2 mass % in 1,2-dimethoxybenzene or in 1,2-dichloroethane, and details of a method for the measurement will be described in the Examples.

In addition to the properties of the high carrier mobility, the compound of the present invention has, as an organic semiconductor material, excellent properties such as high ON/OFF ratio of a drain current by a gate voltage of a transistor.

Moreover, the compound of the present invention is excellent at the chemical stability such as oxidation resistance.

Moreover, since the compound of the present invention, as mentioned later, can be synthesized in a short step using a reaction that is easy to perform in synthetic organic chemistry, it can be used as a practically usable organic semiconductor material that can be industrially manufactured.

With the above reason, the compound of the present invention can be preferably used as the organic semiconductor material.

Specific examples of the compound of the present invention are shown below.

Examples of the compound (1) in which at least one of Xs is oxygen include the following compounds. Since it is not necessary for two Xs being the same elements, the examples include compounds in which one X is other than oxygen.

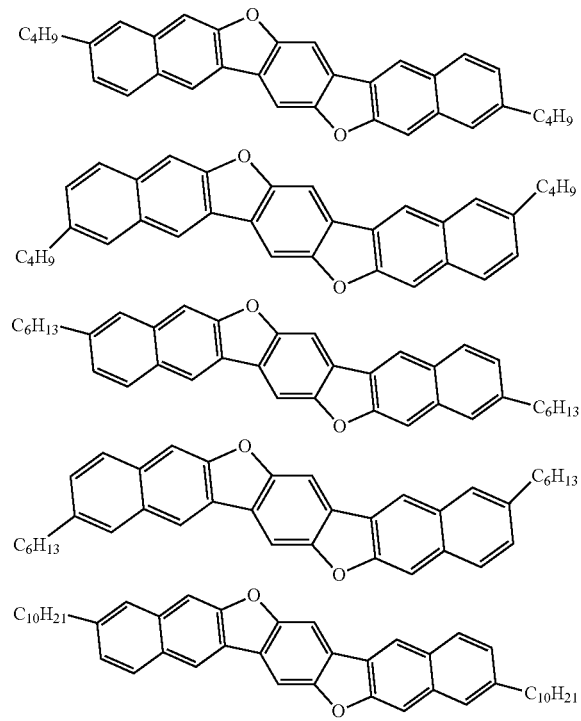

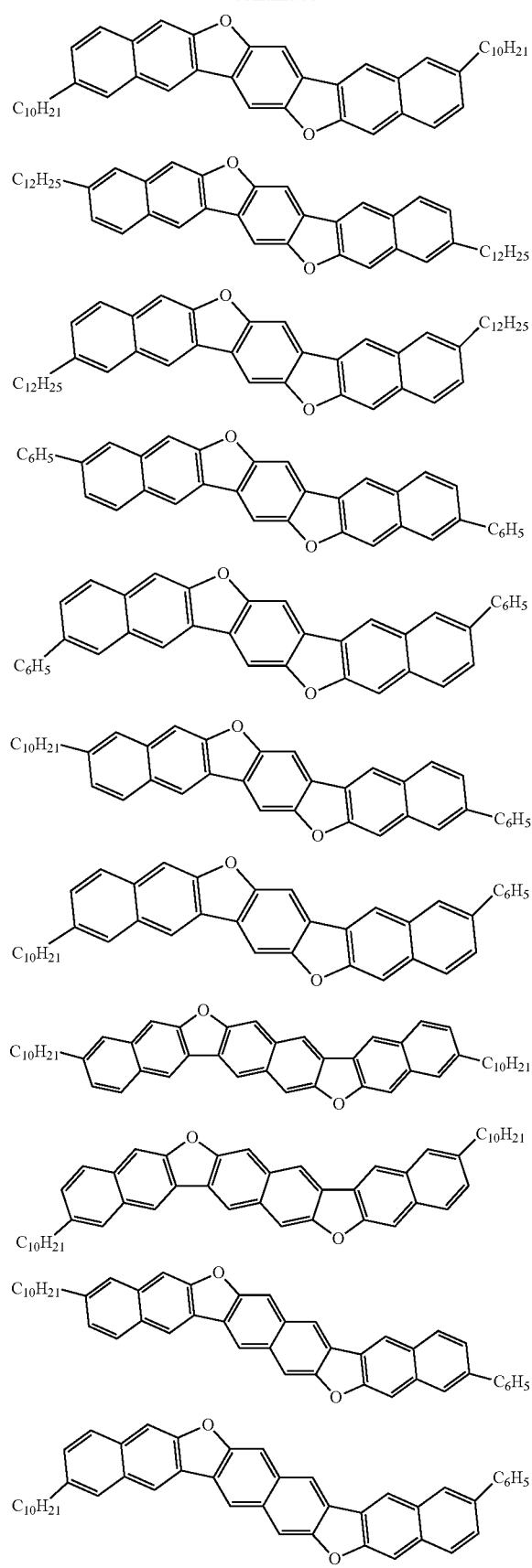
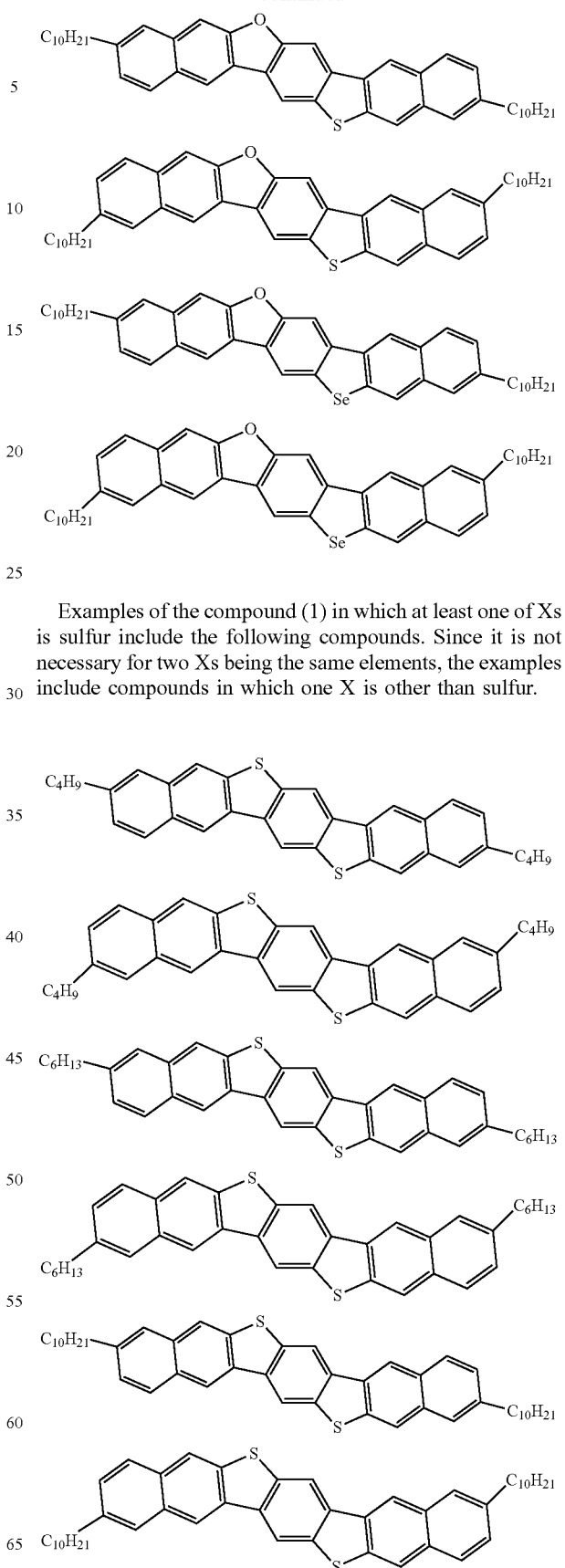
Examples of the compound (1) in which at least one of Xs is sulfur include the following compounds. Since it is not necessary for two Xs being the same elements, the examples include compounds in which one X is other than sulfur.

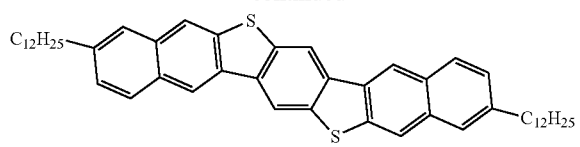
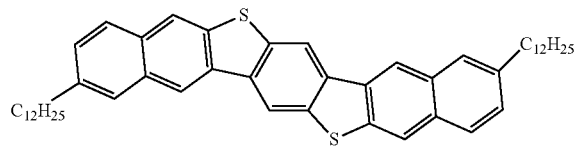
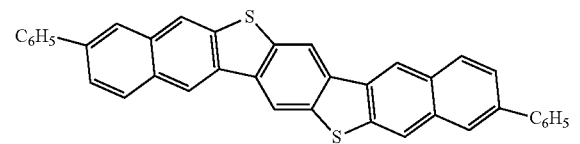
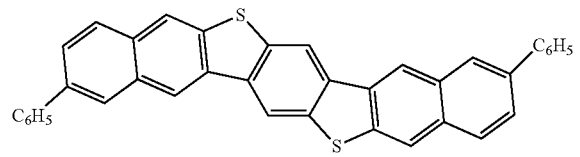
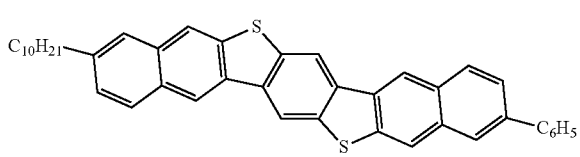
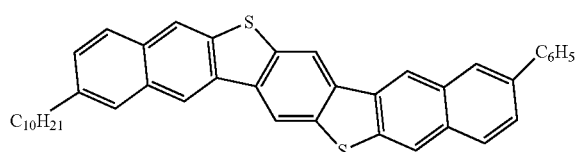
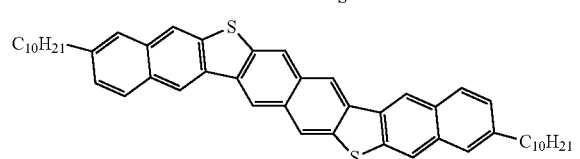
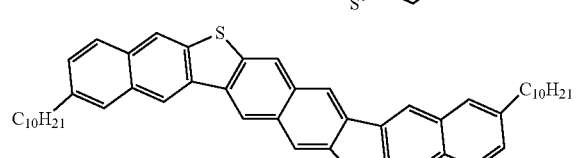
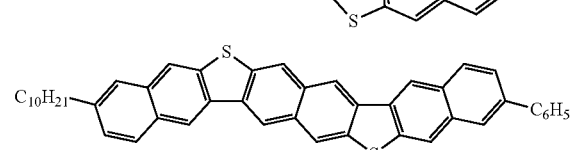
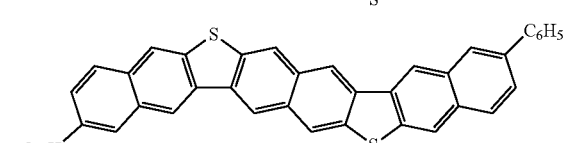
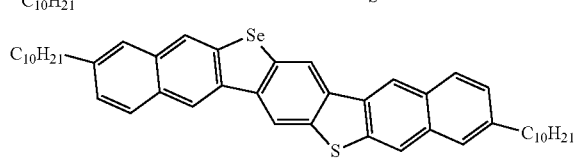
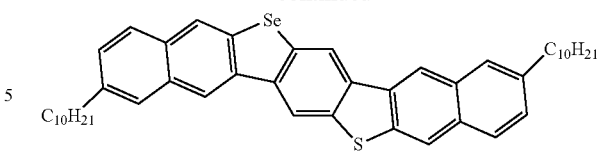
Examples of the compound (1) in which at least one of Xs is selenium include the following compounds. Since it is not necessary for two Xs being the same elements, the examples include compounds in which one X is other than selenium.
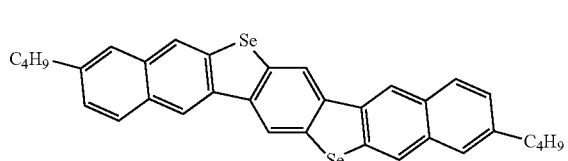
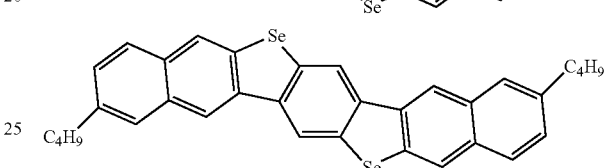
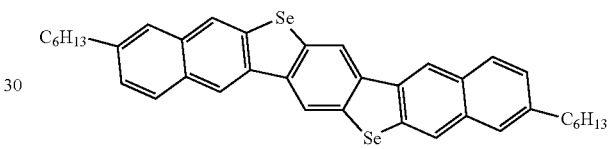
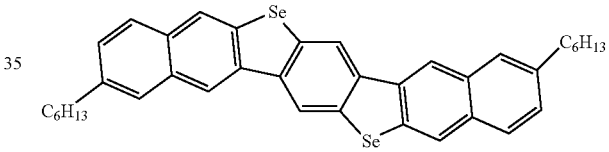
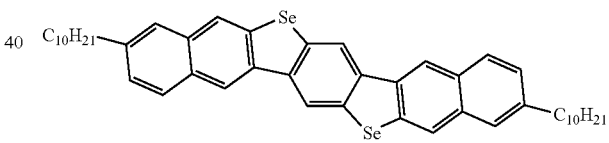
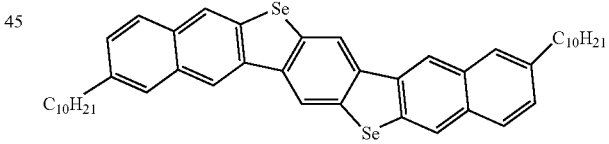
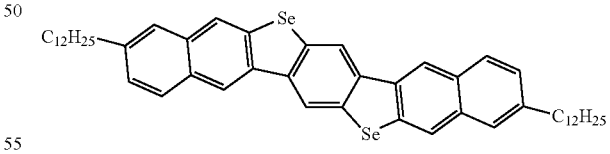
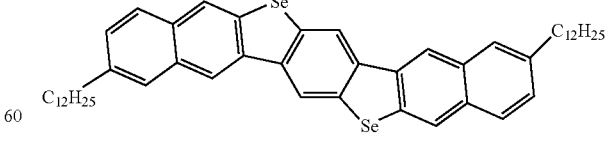
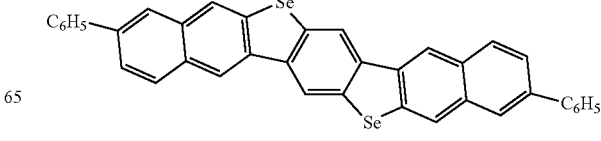

-continued

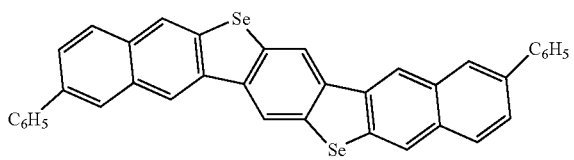

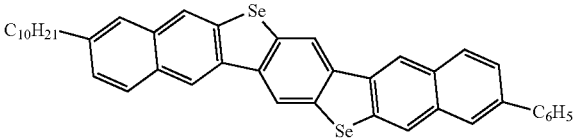

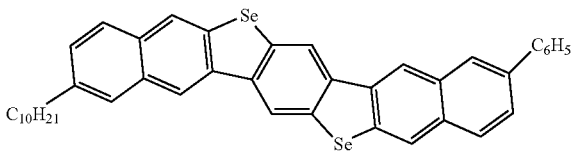

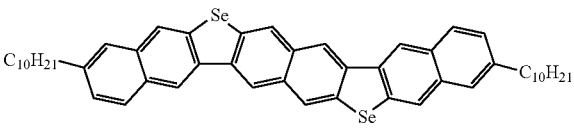

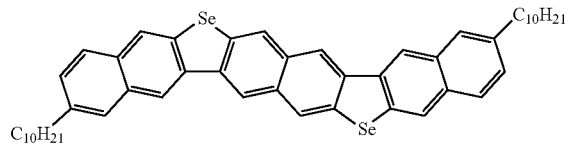

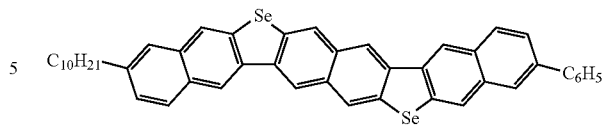

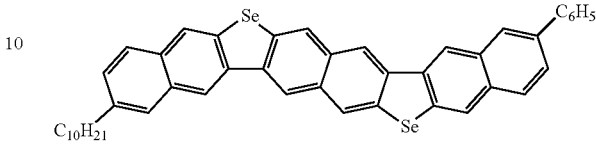

[Method for Producing Compound (1)]

A method for producing the compound of the present invention (1: X=sulfur or selenium) includes; Step 1A of cross-coupling a compound represented by Formula (11) and a compound represented by Formula (12) to obtain a compound represented by Formula (13); Step 2A of deprotecting the methoxy from the compound represented by Formula (13) to obtain a compound represented by Formula (14); Step 3A of allowing the compound represented by Formula (14) to react with N,N-dialkyl carbamoylthiochloride or N,N-dialkyl carbamoylselenochloride to obtain a compound represented by formula (15); and Step 4A of heating the compound represented by Formula (15) to obtain the compound represented by Formula (1).

A method for producing the compound of the present invention (1: X=oxygen) includes; the Step 1A; the Step 2A; and Step 3A' of heating and dehydrating the compound represented by Formula (14) under a zeolite catalyst to obtain the compound represented by Formula (1).

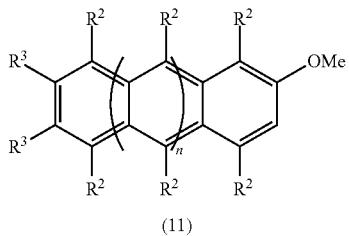 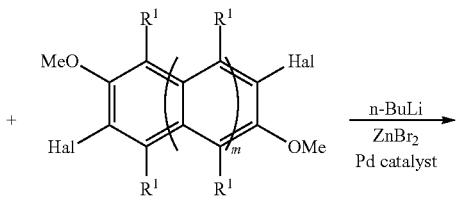

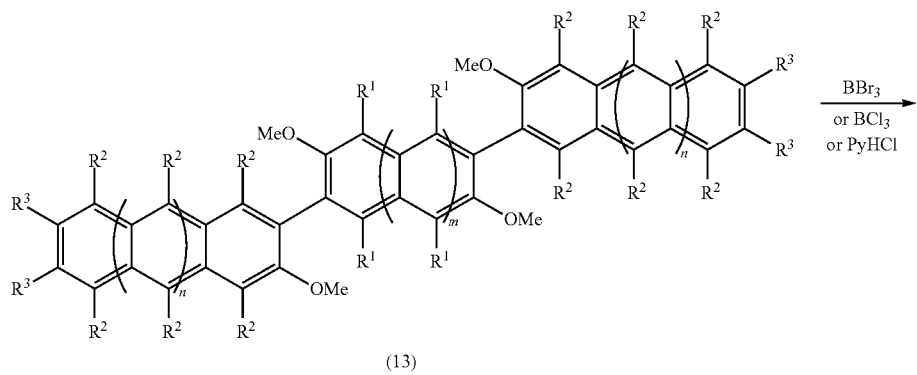

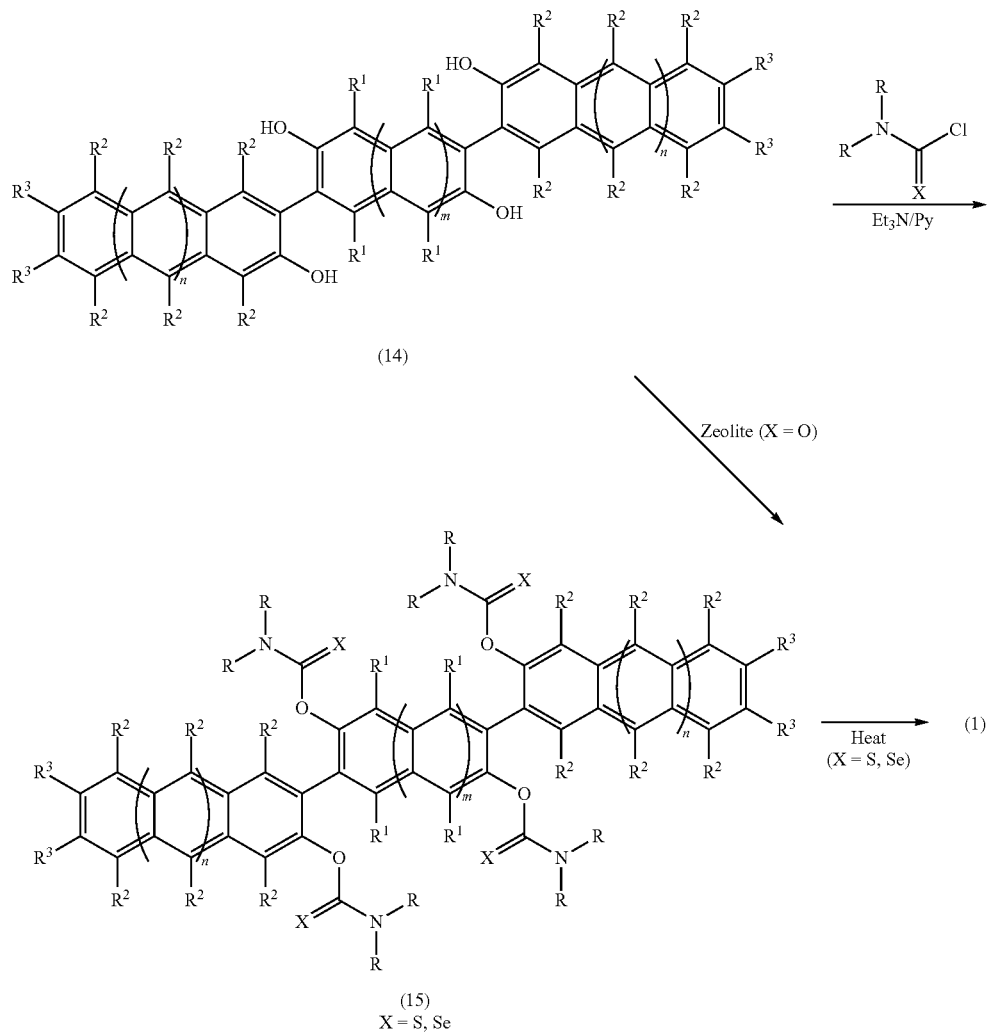

In Formulae (11)-(15), the definitions of m, n and $R^1$-$R^3$ are the same as the corresponding symbols of those in Formula (1) respectively; Hal is bromine or iodine, each R is independently alkyl having 1-3 carbons. In the reaction equations, Me is methyl, n-Bu is normalbutyl, Et is ethyl, Py is pyridine, but these are examples, and the agents used for each reaction are not specifically limited to these.

In each step below, the reaction is preferably carried out in a solution state. As the solvent, for example, it is preferred to use at least one organic solvent selected from the group consisting of a nitrile solvent such as acetonitrile; a halogenated solvent such as dichloromethane, chloroform, chlorobenzene and dichlorobenzene; an ether solvent such as tetrahydrofuran; and an aromatic hydrocarbon solvent such as toluene. Further, when an organometallic compound is added into a solution of Compound (11), it is preferred to add the compound as its solution in an organic solvent such as hexane.

Between the respective steps, a purification may be performed on the obtained compound (crude product) appropriately. Examples of a method for the purification include a method by column chromatography or by re-crystallization.

<Step 1A> (Cross-Coupling)

In Step 1A, Compound (11) and Compound (12) are cross-coupled under existence of an organometallic compound. The amount of Compound (11) for using is normally 2.0 to 3.0 mol based on 1 mol of Compound (12).

Examples of the organometallic compound include n-butyl lithium and s-butyl lithium, and it can be used alone in one kind or in combination of two or more kinds. The amount of the organometallic compound for using is normally 1.05 to 2.10 mol based on 1 mol of Compound (11).

In Step 1A, Compound (13) is synthesized by a known cross-coupling reaction, for example, Suzuki coupling, Stille coupling, Negishi coupling, Tamao coupling, and derivative reaction thereof.

In Step 1A, it is preferred to perform the cross-coupling of Compound (11) in the state of a solution or a suspension. As the solvent, while it could be varied depending on the cross-coupling form, it is preferred to use, for example, at least one organic solvent selected from a group consisting of N,N-dimethylformamide, tetrahydrofuran, toluene and diethylether.

As a catalyst used for the cross-coupling reaction, and as a condition for the reaction (example: a temperature, a time), these could be varied depending on the cross-coupling form, and are not specifically limited.

Examples of the catalyst include a palladium catalyst such as tetrakis(triphenylphosphine)palladium (0), 1,3-bis(diphenylphosphino)propanepalladium (II) dichloride, 1,1'-Bis(diphenylphosphino)ferrocene-palladium (II) dichloride-dichloromethane complex, and tris(dibenzylideneacetone) dipalladium (0) chloroform complex, and also a nickel catalyst such as [1,3-bis(diphenylphosphino)propane]nickel (II) dichloride.

A reaction temperature of Step 1A (example: a temperature of the solution or the suspension) is normally 0 to 140° C., and preferably room temperature to 140° C.; a reaction time is normally 10 min to 24 h, and preferably 1 h to 24 h; and the reaction is normally carried out under ordinary pressure. The reaction temperature could be varied depending on the kind of the coupling. For example, it is 80 to 140° C. in the Stille coupling, 0° C. to room temperature in the Tamao coupling, and 80 to 110° C. in the Suzuki coupling. "Room temperature" means a temperature environment of about 23° C.

<Step 2A> (De-Protection)

In Step 2A, the deprotection of the methoxy on Compound (13) is carried out under existence of a deprotecting agent. A reaction temperature of Step 2A (example: a temperature of the solution) is normally −78° C. to the room temperature, and preferably 0 C.° to the room temperature; a reaction time is normally 1 h to 2 h; and the reaction is normally carried out under ordinary pressure.

Examples of the deprotecting agent include an inorganic compound such as boron tribromide, boron trichloride, aluminum chloride, and an organic compound such as pyridine hydrochloride, and it can be used alone in one kind or in combination of two or more kinds. The amount of the deprotecting agent is normally 4.0 to 4.8 mol based on 1 mol of Compound (13).

<Step 3A>

In Step 3A, Compound (14) is allowed to react with N,N-dialkyl carbamoylthiochloride or N,N-dialkyl carbamoylselenochloride under existence of a base. A reaction temperature of Step 3A (example: a temperature for heating the solution) is normally 60 to 80 C.°; a reaction time is normally 10 h to 48 h; and the reaction is normally carried out under ordinary pressure.

Each carbon number of the two alkyls in N,N-dialkyl carbamoylthiochloride and N,N-dialkyl carbamoylselenochloride is independently 1 to 3, and preferably 1 to 2.

Examples of the N,N-dialkyl carbamoylthiochloride include N,N-dimethyl carbamoylthiochloride and N,N-diethyl carbamoylthiochloride. Examples of the N,N-dialkyl carbamoylselenochloride include N,N-dimethyl carbamoylselenochloride and N,N-diethyl carbamoylselenochloride. The amount of N,N-dialkyl carbamoylthiochloride or N,N-dialkyl carbamoylselenochloride for using is normally 6.0 to 8.0 mol based on 1 mol of Compound (14).

Examples of the base include triethylamine, pyridine and sodium hydride, and it can be used alone in one kind or in combination of two or more kinds. As the amount of the base for using, triethylamine is normally 4.0 to 8.0 mol, and preferably 6.0 to 7.5 mol, and pyridine is normally 5 to 100 mol, and preferably 20 to 60 mol, based on 1 mol of Compound (14).

<Step 4A> (Cyclization)

In Step 4, Compound (15) is subjected to heating and cyclization to obtain the Compound (1), which is the compound of the present invention. The heating temperature of Step 4A is normally 300 to 320° C.; and the reaction time is normally 4 h to 6 h. In this step, the heating can be performed under an atmosphere of an inert gas without solvent, or in a solvent having a boiling point of not less than 300° C.

<Step 3A'> (Dehydrational Cyclization)

In Step 3A', zeolite is added to the solution of Compound (14), and dehydration and cyclization are performed, to obtain Compound (1), which is the compound of the present invention. The reaction temperature of Step 3A' (example: a temperature for heating the solution) is normally 160 to 180° C.; the reaction time is normally 8 h to 20 h, and preferably 10 h to 16 h; and the reaction is normally carried out under ordinary pressure.

In the above mentioned methods for producing the compound of the present invention, since the compound of the present invention shows high solubility in a solvent, the crude compound as synthesized can be easily purified with an easy method such as a column chromatography or a re-crystallization.

Furthermore for the usage of the organic semiconductor, since an extra high purity is required, it is useful to perform a vacuum sublimating purification to the compound of the present invention obtained with the above mentioned production methods, as necessary.

[Film of Organic Semiconductor Film or the Like]

A film of the present invention (example: an organic semiconductor film) includes the compound of the present invention, namely at least one selected from the Compound (1). Since the compound of the present invention shows high solubility in a solvent, and therefore with applying or printing a solution (hereinafter, also referred to as "organic semiconductor solution") in which the compounds are dissolved into the solvent onto a substrate, a film (example: organic semiconductor film) having excellent surface uniformity can be formed.

Examples of the solvent used for preparation of the organic semiconductor solution include an organic solvent such as pentane, hexane, heptane, diethyl ether, t-butyl methyl ether, tetrahydrofuran, methanol, ethanol, isopropanol, ethyl acetate, ethyl lactate, dioxane, benzene, toluene, xylene, dichloromethane, chloroform, 1,2-dichloroethane, dichlorobenzene, acetonitrile, acetone, cyclohexane, cyclopentanone, cyclohexanone, γ-butyrolactone, butyl cellosolve, N-methyl-2-pyrrolidone, N,N-dimethylformamide (DMF), 1,2-dimethoxybenzene, 3-phenoxytoluene, anisole, tetralin, o-dichlorobenzene and dimethyl sulfoxide; water; or a mixture of two or more kinds thereof.

The concentration of the compound of the present invention in the organic semiconductor solution is preferably 0.05 to 10 mass %, and more preferably 0.1 to 5 mass %. Since the compound of the present invention shows high solubility in a solvent, it is possible to prepare a high concentration solution. Here, the high concentration solution means an organic semiconductor solution of which the concentration of the compound of the present invention is 0.1 mass % or more.

With the excellent solubility of the compound of the present invention in a solvent, it is possible to prepare the organic semiconductor solution at varied concentration, and therefore a crystallization degree of the obtained film can be variably adjusted. When the crystallization degree of the film is changed, the carrier mobility is changed with being influenced by the crystallization degree. Accordingly, with the present invention, a crystallinity can be easily adjusted within wide range including crystalline state to amorphous state, and it is stably possible to reproduce the required property of the device, such as the thickness of the organic semiconductor film and the carrier mobility.

Furthermore, the film formation may be performed using a resin composition including the compound of the present invention and a polymer compound. A content of the polymer compound in the resin composition is normally 1 to 99 mass %, preferably 5 to 90 mass %, and more preferably 5 to 80 mass %. Furthermore, a content of the solvent in the resin composition is appropriately fixed, so that the content of the compound of the present invention and the polymer compound could be within the range, and the resin composition could have suitable viscosity for the film formation.

Examples of the polymer compound include a thermoplastic polymer and a thermo-setting polymer. The embodiments include polyester, polyamide, polystyrene, polymethacrylic acid, polyacrylic acid, polyethylene, polypropylene, polycycloolefin, polyvinyl chloride, polyvinylidene chloride, polyvinyl acetate, polycarbonate, a phenolic resin, a polyurethane resin, an epoxy resin, a melamine resin, polytetrafluoroethylene, polyacethylene, polypyrrole, and polyarylene vinylene. Also a conductive polymer may be used as the polymer compound. Examples of the conductive polymer include polythiophene, polypyrrole and polyaniline.

The thickness of the film of the present invention can be appropriately selected according to a desired usage. For example, the thickness of the organic semiconductor film used for the organic semiconductor device is preferably 10 to 1,000 nm, and more preferably 10 to 200 nm.

Examples of a method for forming the film of the present invention include various methods.

Examples of an applying method include a spin coating method, a dip coating method, and a blade method. Moreover, the edge-cast method (see Appl. Phys. Exp. 2, 111501 (2009)) and the gap-cast method (see Adv. Mater. 23, 1626 (2011).) as developed by the present inventors, and classified into the application method as described later in Examples are also effective.

Examples of the printing method include screen printing, inkjet printing, lithography, intaglio printing and letterpress printing. Among the printing methods, inkjet printing to be performed by a printer in which the solution of the compound of the present invention is directly used as ink is an easy method, and therefore preferred.

No limitation is taken to perform a film formation method other than the above, such as the vapor deposition method, for example.

The temperature when performing the film formation is not specifically limited, and normally room temperature to 200° C., and preferably 50 to 150° C. The temperature here, for example of the case of the applying method or the printing method, is a temperature for heating the organic semiconductor solution, an temperature of the atmosphere, or a temperature for heating the substrate used for the film formation. The solution temperature, the atmosphere temperature, the substrate temperature of the above may be different with each other. For a film formation without using the above solution, for example of the deposition method, it means the temperature for heating the substrate used for the film formation.

In the case that the organic semiconductor film is directly used as a part of the organic semiconductor device, the patterning is preferably performed by the printing method, and further preferred is using the high concentration solution of the compound of the present invention for the printing method. When using the high concentration solution, the inkjet printing, mask printing, screen printing, and offset printing or the like can be utilized. Further, the production of the organic semiconductor film by the printing method does not require the process of heating or of vacuum and makes an assembly-line operation possible, and therefore it contributes to cost reduction and an increase in flexibility for changing steps. Also the production of the organic semiconductor film by the printing method contributes to simplification of the device circuit, an improvement in its productivity, and cost reduction and weight reduction of the device. From the above viewpoints, the compound of the present invention showing high solubility in a solvent is excellent.

[Organic Semiconductor Device]

An organic semiconductor device of the present invention includes the organic semiconductor film and an electrode. Specifically, the organic semiconductor device can be provided by combining the organic semiconductor film with a device having other semiconducting property. Examples of the device having other semiconducting property include a rectifier, a thyristor performing switching action, a TRIAC and a DIAC.

The organic semiconductor device of the present invention can be used as a display device, and especially a display device all parts of which are made with organic compounds is useful.

Examples of the display device include a flexible sheet-shaped display device (electronic paper, IC card tag), a liquid crystal display device and an electroluminescence (EL) device. The display devices can be prepared by forming, on an insulating substrate formed of a polymer and showing flexibility, the organic semiconductor film of the invention and at least one layer including a constituent for allowing function of the film. The display device prepared by such a method has flexibility, and therefore can be carried by putting the device into a pocket of clothes, a purse or the like.

Examples of the display device also include a proper identification code response system. The proper identification code response system reacts with electromagnetic waves having a specific frequency or a specific code, and responds to electromagnetic waves including a proper identification code. The proper identification code response system is used as a means for identifying a document or a person in a reusable passenger ticket or a membership card, a means of payment and settlement, a seal for identification of a parcel or merchandise, a role of a label or stamp, company or administrative services, or the like.

The proper identification code response system has, on a glass substrate or an insulating substrate formed of the polymer and showing flexibility, an aerial for receiving a signal in synchronizing with the signal, and the organic semiconductor device of the present invention that operates with received electric power and sends an identification signal.

<Organic Field Effect Transistor (FET)>

Examples of the organic semiconductor device of the present invention include an organic field effect transistor (FET). The organic FET of the present invention can also be used in a combination with a liquid crystal display device and an electroluminescence (EL) device.

The organic FET of the present invention has a substrate, a gate electrode, a gate insulating film, a source electrode, a drain electrode and an organic semiconductor layer, and the organic semiconductor layer is constituted of the organic semiconductor film of the present invention. Moreover, the organic FET of the present invention may have a carrier injection layer in order to improve carrier injection efficiency.

In the organic FET, a carrier is induced on an interface of the organic semiconductor layer on the gate insulating film by controlling voltage applied to the gate electrode, and an electric current flowing through the source electrode and the drain electrode is controlled, thereby performing the switching action.

In the organic FET, the carrier mobility can be determined from a drain current/gate voltage curve obtained by measuring an electric current between the source electrode and the drain electrode while changing a drain voltage and a gate voltage. Furthermore, ON/OFF action of the drain current by the gate voltage can also be observed.

In general, structure of the organic FET is broadly classified into bottom gate type structure and top gate type structure, and each structure is further classified into top contact structure and bottom contact structure.

As the organic FET, an embodiment in which the gate electrode is formed on the substrate, and the gate insulating film and the organic semiconductor layer are further formed in this order is referred to as the bottom gate type structure; and structure in which the organic semiconductor layer, the gate insulating film and the gate electrode are formed on the substrate in this order is referred to as the top gate type structure.

Moreover, as the organic FET, an embodiment in which the source electrode and the drain electrode are arranged on a lower part of the organic semiconductor layer (on substrate side) is referred to as a bottom contact type FET; and an embodiment in which the source electrode and the drain electrode are arranged on an upper part of the organic semiconductor layer (on side opposite to substrate by interposing organic semiconductor layer) is referred to as a top contact type FET. From a viewpoint of carrier injection between the source electrode and the organic semiconductor layer and between the drain electrode and the organic semiconductor layer, the top contact type structure is superior in organic FET characteristics to the bottom contact type structure in many cases.

FIG. 1 shows a cross-sectional view of an organic FET having each of a bottom gate-top contact type (a), a bottom gate-bottom contact type (b), a top gate-top contact type (c) and a top gate-bottom contact type (d). However, the organic FET of the invention is not limited to the structure of the organic FET described above, but may have publicly known organic FET structure. Moreover, the organic FET of the invention may also adopt vertical organic FET structure.

Examples of the substrate include various substrates. Specific examples include a glass substrate, a metal substrate such as gold, copper and silver substrates, a crystalline silicon substrate, an amorphous silicon substrate, a triacetyl cellulose substrate, a norbornene substrate, a polyester substrate such as a polyethylene terephthalate substrate, a polyvinyl chloride substrate, a polypropylene substrate and a polyethylene substrate.

Examples of materials of the gate electrode include an inorganic material such as Al, Ta, Mo, Nb, Cu, Ag, Au, Pt, In, Ni, Nd, Cr, silicon including polysilicon, amorphous silicon and highly doped silicon, tin oxide, indium oxide and an indium tin compound (indium tin oxide: ITO); and an organic material such as a conductive polymer. However, the conductive polymer may be treated so as to improve conductivity by addition of impurities.

Examples of materials of the gate insulating film include an inorganic material such as $SiO_2$, $SiN$, $Al_2O_3$ and $Ta_2O_5$; and a polymer material such as polyimide and polycarbonate.

A surface of the gate insulating film and the substrate can be subjected to surface treatment using a publicly known silane coupling agent, for example, a silane coupling agent having an alkyl group, such as hexamethyldisilazane (HMDS), octadecyltrichlorosilane (OTS), decyltriethoxysilane (DTS) and octadecyltriethoxysilane (ODSE), or a silane coupling agent having a fluoroalkyl group, such as triethoxytridecafluorooctylsilane (F-SAM). If the surface is subjected to suitable surface treatment using HMDS, OTS, DTS, ODSE, F-SAM or the like, an increase in a grain diameter of crystal constituting an organic FET layer, an improvement of crystallinity, an improvement of molecular orientation or the like is generally observed. As a result, the carrier mobility and the ON/OFF ratio are improved, and a threshold voltage tends to decrease.

As materials of the source electrode and the drain electrode, materials of a kind same with the materials of the gate electrode can be used, and may be identical with or different from the materials of the gate electrode, or different kinds of materials may be laminated.

The carrier injection layer is arranged, as required, in the form of contact with any of the source electrode, the drain electrode and the organic semiconductor layer in order to improve the carrier injection efficiency. The carrier injection layer is formed by using tetrafluorotetracyanoquinodimethane (F4TCNQ), hexaazatriphenylenehexacarbonitrile (HAT-CN), molybdenum oxide or the like.

EXAMPLES

The present invention will be more specifically described by way of Examples below, but the present invention is in no way limited to the Examples. A method for measuring physical properties of a synthetic compound is as follows.

A melting point was measured using Toledo MP70 Automatic Melting-Point System made by Mettler-Toledo International Inc.

A $^1$H-NMR spectrum and a $^{13}$C-NMR spectrum were measured using ECA-600 and ECS400 Spectrometer made by JEOL Ltd.

For an elemental analysis, JM10 MICRO CORDER made by J-SCIENCE LAB Co., Ltd. was used.

For a mass analysis, JMS-T100LC APCI/ESI Mass Spectrometer made by JEOL Ltd. and ultraflex III TOF/TOF made by Bruker Daltonics Inc. were used.

In addition, in each title compound in the following Examples, all of alkyl are a straight-chain group.

Example 1

Synthesis of 2,10-didecyldinaphtho[2,3-d:2',3'-d'] benzo[1,2-b:4,5-b']difuran (First Step)

Synthesis of 3,3'-(2,5-dimethoxy-1,4-phenylene)bis (6-decyl-2-methoxynaphthalene)

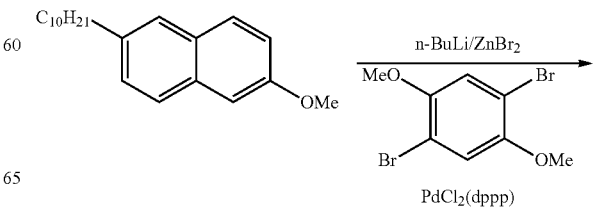

-continued

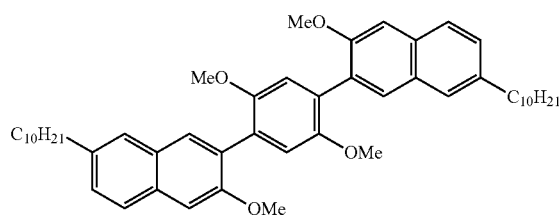

2-Decyl-6-methoxynaphthalene (10.3 g, 34.5 mmol) was dissolved in 138 ml of tetrahydrofuran (THF), and then stirred at 0° C. Hereinto, n-butyllithium (1.65 M hexane solution) (23.0 ml, 38.0 mmol) was added dropwise and stirred at 0° C. for 2 hours. To this solution, zinc bromide (1.0 M THF solution) (38.0 ml, 38 mmol) was added at 0° C., then the temperature was put back at room temperature and the stirring was kept for 1 hour. To the obtained light-yellow colored solution, 1,4-dibromo-2,5-dimethoxybenzene (4.26 g, 14.4 mmol) and 1,3-bis(diphenylphosphino)propane palladium (II) dichloride ($PdCl_2$ (dppp)) (610 mg, 1.04 mmol) were added, and the reaction solution was stirred at 50° C. for 12 hours. The reaction solution was poured into an excess amount of water, extracted with ethyl acetate, the organic layer was washed with saturated saline solution, and then dried with anhydrous magnesium sulfate. The organic layer was filtered to remove the drying agent, then the solvent was removed therefrom by distillation under reduced pressure to remain approximately 40 ml of the solvent, methanol and chloroform were added thereto for performing re-precipitation, and the resulted precipitate was filtered to obtain the titled compound in white solid (6.38 g, 9.45 mmol). The solution filtered off was concentrated under reduced pressure, and the remained residue was purified with silica gel column chromatography (hexane:chloroform=80:20 to 50:50 (volume ratio)), to collect the titled compound (1.67 g, 2.47 mmol). The total yield summing up both was 83%. The physical property values of the obtained compound are shown as follows.

Melting point: 167.3-167.9° C. $^1$H NMR (600 MHz, $CDCl_3$): δ0.89 (t, J=6.6 Hz, 6H, $CH_3$), 1.27-1.35 (m, 28H, $(CH_2)_7$), 1.69 (quin, J=7.2 Hz, 4H, $ArCH_2CH_2$), 2.75 (t, J=7.2 Hz, 4H, $ArCH_2$), 3.75 (s, 6H, $OCH_3$), 3.94 (s, 6H, $OCH_3$), 6.99 (s, 2H, ArH), 7.22 (s, 2H, ArH), 7.30 (d, J=8.4 Hz, 2H, ArH), 7.56 (s, 2H, ArH), 7.70 (d, J=8.4 Hz, 2H, ArH), 7.74 (s, 2H, ArH). $^{13}$C NMR (150 MHz, $CDCl_3$): δ14.27, 22.84, 29.47, 29.49, 29.73, 29.77 (two carbons), 31.71, 32.05, 36.11, 55.85, 56.72, 105.51, 115.37, 126.32, 126.45, 127.82, 127.95, 128.95, 129.73, 130.20, 132.66, 138.39, 151.35, 155.51. TOF HRMS (APCI+): Calcd for $C_{50}H_{67}O_4$ [M+H] 731.5039, found, 731.5031. Anal. Calcd for $C_{50}H_{66}O_4$: C, 82.15; H, 9.10. Found C, 82.27; H, 9.11.

(Second Step)

Synthesis of 2,5-bis(7-decyl-3-hydroxynaphthalene-2-yl)benzene-1,4-diol

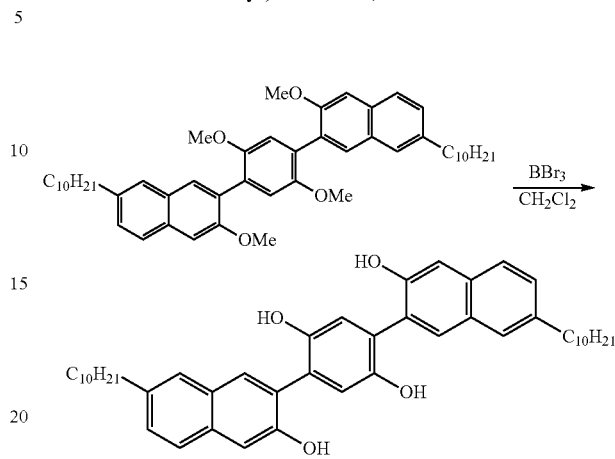

To 3,3'-(2,5-Dimethoxy-1,4-phenylene)bis(6-decyl-2-methoxynaphthalene) (10.0 g, 22.2 mmol) obtained in the first step, as its solution in dichloromethane (89 ml), boron tribromide (1.0 M dichloromethane solution) (98.0 ml, 98.0 mmol) was added at 0° C., and the mixture was stirred at room temperature for 2 hours. The reaction solution was poured into an ice water, extracted with ethyl acetate, the organic layer was washed with saturated saline solution, and then dried with anhydrous magnesium sulfate. The organic layer was filtered to remove the drying agent, then the solvent was removed therefrom by distillation under reduced pressure to remain approximately 20 ml of the solvent, acetone and dichloromethane were added thereto for performing re-precipitation, and the resulted precipitate was filtered to obtain the titled compound in white solid (7.07 g, 17.9 mmol). The yield was 81%. The physical property values of the obtained compound are shown as follows.

Melting point: 230.0-231.0° C. $^1$H NMR (600 MHz, acetone-$d_6$): δ0.91 (t, J=7.2 Hz, 6H, $CH_3$), 1.26-1.42 (m, 28H, $(CH_2)_7$), 1.76 (quin, J=7.2 Hz, 4H, $ArCH_2CH_2$), 2.80 (t, J=7.2 Hz, 4H, $ArCH_2$), 2.89 (brs, 4H, OH), 7.11 (s, 2H, ArH), 7.36 (d, J=8.4 Hz, 2H, ArH), 7.39 (s, 2H, ArH), 7.70 (s, 2H, ArH), 7.71 (d, J=8.4 Hz, 2H, ArH), 7.86 (s, 2H, ArH). $^{13}$C NMR (150 MHz, THF-$d_8$): δ15.04, 24.16, 30.88, 30.90, 31.15, 31.21 (two carbons), 33.09, 33.47, 37.39, 111.98, 120.90, 127.11, 127.56, 128.29, 128.82, 130.35, 130.67, 131.61, 134.51, 138.83, 149.30, 153.91. TOF HRMS (APCI+): Calcd for $C_{46}H_{59}O_4$ [M+H] 675.4413, found, 675.4412.

(Third Step)

Synthesis of 2,10-didecyldinaphtho[2,3-d:2',3'-d']benzo[1,2-b:4,5-b']difuran

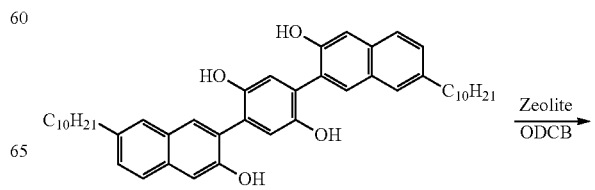

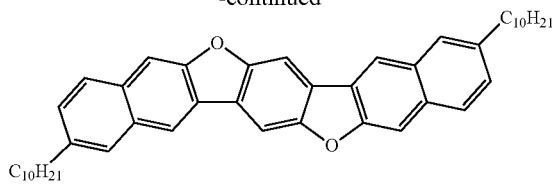

To 2,5-bis(7-decyl-3-hydroxynaphthalene-2-yl)benzene-1,4-diol (810 mg, 1.20 mmol), as its suspension in o-dichlorobenzene (ODCB; 24 mL), zeolite (324 mg) was added, and the mixture was stirred at 160° C. for 20 hours. The solution was filtered without cooling to remove the zeolite catalyst, then methanol was added thereto, and the obtained product material in light-yellow colored solid was isolated by vacuum filtration. The obtained amount was 579 mg, at 76% of yield.

Melting point: 316-317° C. $^1$H NMR (600 MHz, CDCl$_2$CDCl$_2$, 100° C.): δ 0.88 (t, J=7.2 Hz, 6H, CH$_3$), 1.26-1.43 (m, 28H, (CH$_2$)$_7$), 1.77 (quin, J=7.8 Hz, 4H, ArCH$_2$CH$_2$), 2.82 (t, J=7.8 Hz, 4H, ArCH$_2$), 7.39 (d, J=8.4 Hz, 2H, ArH), 7.81 (s, 2H, ArH), 7.87 (d, J=8.4 Hz, 2H, ArH), 7.89 (s, 2H, ArH), 8.13 (s, 2H, ArH), 8.38 (s, 2H, ArH). TOF HRMS (APCI+): Calcd for C$_{46}$H$_{55}$O$_2$ [M+H] 639.4202, found, 639.4199. Anal. Calcd for C$_{46}$H$_{54}$O$_2$: C, 86.47; H, 8.52. Found C, 86.56; H, 8.53.

Example 2

Synthesis of 2,10-didecyldinaphtho[2,3-d:2',3'-d']benzo[1,2-b:4,5-b']dithiophene (First Step)

Synthesis of O,O'-(2,5-bis(7-decyl-3-((dimethylcarbamoylthioyl)oxy)naphthalene-2-yl)-1,4-phenylene)bis(dimethylcarbamothioate)

To 2,5-bis(7-decyl-3-hydroxynaphthalene-2-yl)benzene-1,4-diol (1.69 g, 2.50 mmol) obtained in the second step in Example 1, as its solution in tetrahydrofuran (20 ml), triethylamine (2.1 ml), pyridine (5.3 ml), N,N-dimethylcarbamoylthiochloride (2.47 g, 20.0 mmol) were added, and the mixture was stirred at 65° C. for 20 hours. This solution was concentrated under reduced pressure, and the obtained crude material was purified by silica gel column chromatography with a mixture solvent of hexane and ethyl acetate (hexane:ethyl acetate=95:5 to 80:20 (volume ratio)) as a developing solvent, to obtain the titled compound in white solid (1.84 g, 1.80 mmol). The yield was 72%. The physical property values of the obtained compound are shown as follows.

$^1$H NMR (600 MHz, CDCl$_3$): δ0.88 (t, J=6.6 Hz, 6H, CH$_3$), 1.26-1.34 (m, 28H, (CH$_2$)$_7$), 1.69 (quin, J=7.8 Hz, 4H, ArCH$_2$CH$_2$), 2.76 (t, J=7.8 Hz, 4H, ArCH$_2$), 2.96 (s, 6H, NH$_3$), 3.14 (s, 6H, NH$_3$), 3.23 (s, 6H, NH$_3$), 3.38 (s, 6H, NH$_3$), 7.35 (d, J=8.4 Hz, 2H, ArH), 7.37 (s, 2H, ArH), 7.59 (s, 2H, ArH), 7.60 (s, 2H, ArH), 7.76 (d, J=8.4 Hz, 2H, ArH), 7.91 (s, 2H, ArH). $^{13}$C NMR (150 MHz, CDCl$_3$): δ14.26, 22.82, 29.45, 29.47, 29.69, 29.77 (two carbons), 31.55, 32.03, 36.20, 38.57, 39.26, 43.11, 43.52, 121.32, 126.37, 126.68, 127.58, 128.39, 129.04, 130.42, 131.31, 131.38, 131.67, 140.72, 148.72, 148.93, 187.11, 187.35. TOF HRMS (APCI+): Calcd for C$_{58}$H$_{79}$N$_4$O$_4$S$_4$ [M+H] 1023.4984, found, 1023.4990. Anal. Calcd for C$_{58}$H$_{78}$N$_4$O$_4$S$_4$: C, 68.06; H, 7.68; N, 5.47. Found C, 67.99; H, 7.68; N, 5.43.

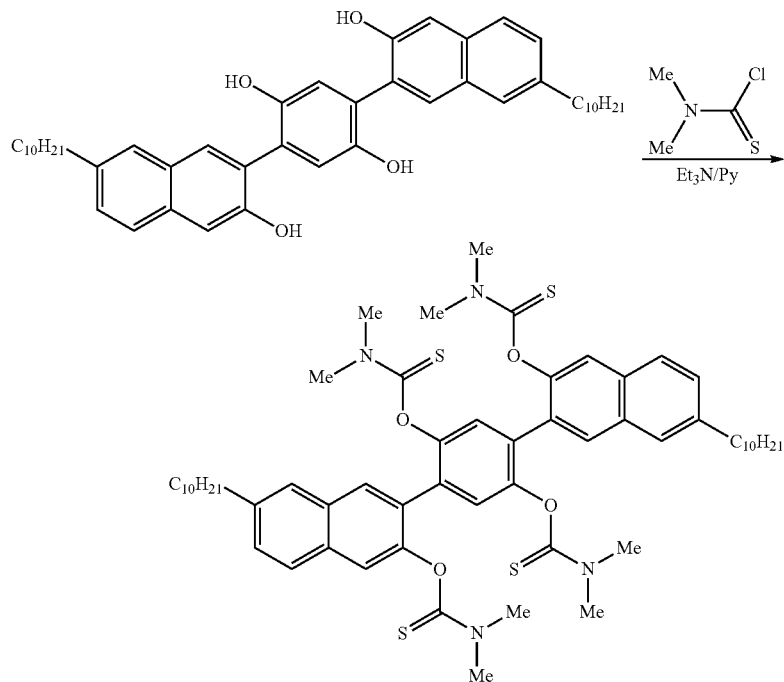

(Second Step)

Synthesis of 2,10-didecyldinaphtho[2,3-d:2',3'-d']benzo[1,2-b:4,5-b']dithiophene

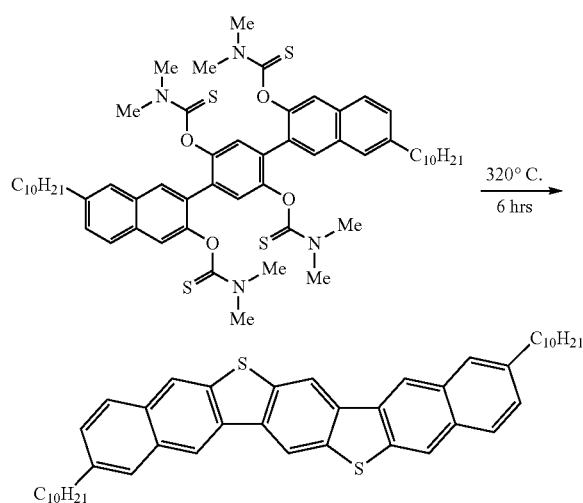

O,O'-(2,5-Bis(7-decyl-3-((dimethylcarbamoylthioyl)oxy)naphthalene-2-yl)-1,4-phenylene)bis(dimethylcarbamothioate) (1.64 g, 1.60 mmol) obtained in the first step of this example was sealed in a Pyrex (registered trademark) tube, and then heated at 320° C. for 6 hours. After the temperature was put back at room temperature, the resulted material was re-crystallized in a mixture solvent of toluene and 1,1,2,2-tetrachloroethane to obtain the titled compound in yellow solid (398 mg, 0.593 mmol). The yield was 37%. The physical property values of the obtained compound are shown as follows.

Melting point: 285 to 286° C. (TG-DTA). $^1$H NMR (600 MHz, CDCl$_2$CDCl$_2$, 100° C.): δ0.89 (t, J=6.6 Hz, 6H, CH$_3$), 1.26-1.44 (m, 28H, (CH$_2$)$_7$), 1.78 (quin, J=7.2 Hz, 4H, ArCH$_2$CH$_2$), 2.83 (t, J=7.2 Hz, 4H, ArCH$_2$), 7.39 (d, J=8.4 Hz, 2H, ArH), 7.80 (s, 2H, ArH), 7.81 (d, J=8.4 Hz, 2H, ArH), 8.21 (s, 2H, ArH), 8.58 (s, 2H, ArH), 8.60 (s, 2H, ArH). TOF HRMS (APCI+): Calcd for C46H55S2 [M+H] 671.3745, found, 671.3743. Anal. Calcd for C$_{46}$H$_{54}$S$_2$: C, 82.33; H, 8.11. Found: C, 82.33; H, 7.98.

Example 3

Synthesis of 3,11-didecyldinaphtho[2,3-d:2',3'-d']benzo[1,2-b:4,5-b']difuran (First Step)

Synthesis of 3,3'-(2,5-dimethoxy-1,4-phenylene)bis(7-decyl-2-methoxynaphthalene)

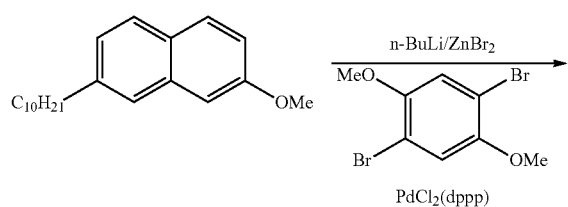

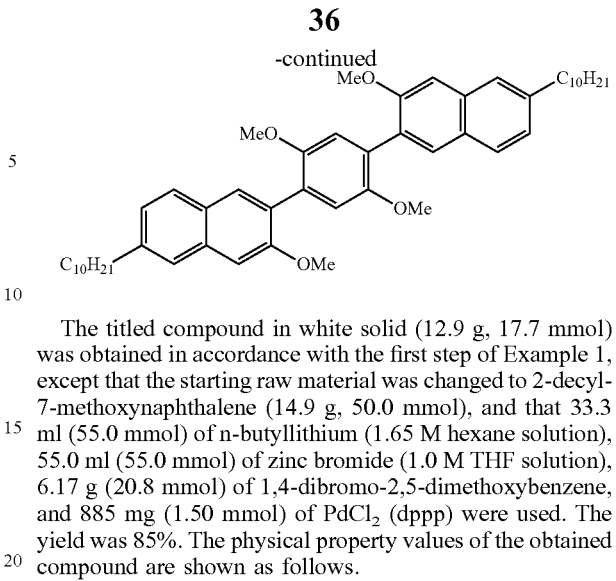

The titled compound in white solid (12.9 g, 17.7 mmol) was obtained in accordance with the first step of Example 1, except that the starting raw material was changed to 2-decyl-7-methoxynaphthalene (14.9 g, 50.0 mmol), and that 33.3 ml (55.0 mmol) of n-butyllithium (1.65 M hexane solution), 55.0 ml (55.0 mmol) of zinc bromide (1.0 M THF solution), 6.17 g (20.8 mmol) of 1,4-dibromo-2,5-dimethoxybenzene, and 885 mg (1.50 mmol) of PdCl$_2$ (dppp) were used. The yield was 85%. The physical property values of the obtained compound are shown as follows.

Melting point: 120.8-122.0° C. $^1$H NMR (600 MHz, CDCl$_3$): δ0.89 (t, J=6.6 Hz, 6H, CH$_3$), 1.26-1.36 (m, 28H, (CH$_2$)$_7$), 1.71 (quin, J=6.6 Hz, 4H, ArCH$_2$CH$_2$), 2.77 (t, J=6.6 Hz, 4H, ArCH$_2$), 3.74 (s, 6H, OCH$_3$), 3.94 (s, 6H, OCH$_3$), 6.98 (s, 2H, ArH), 7.19 (s, 2H, ArH), 7.20 (d, J=7.8 Hz, 2H, ArH), 7.56 (s, 2H, ArH), 7.71 (d, J=7.8 Hz, 2H, ArH), 7.76 (s, 2H, ArH). $^{13}$C NMR (150 MHz, CDCl$_3$): δ14.32, 22.87, 29.48, 29.52, 29.74, 29.80 (two carbons), 31.62, 32.09, 36.36, 55.84, 56.74, 105.24, 115.41, 125.19, 125.45, 127.21, 127.64, 127.76, 128.89, 130.39, 134.51, 141.04, 151.34, 156.09. TOF HRMS (APCI+): Calcd for C50H67O4 [M+H] 731.5039, found, 731.5031. Anal. Calcd for C$_{50}$H$_{66}$O$_4$: C, 82.15; H, 9.10. Found C, 81.89; H, 9.01.

(Second Step)

Synthesis of 2,5-bis(6-decyl-3-hydroxynaphthalene-2-yl)benzene-1,4-diol

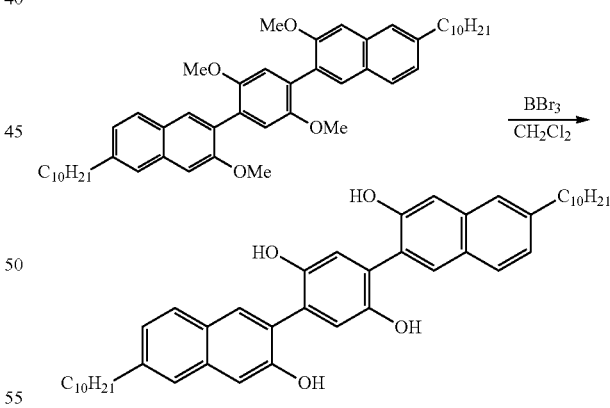

The titled compound in white solid (2.88 g, 4.26 mmol) was obtained in accordance with the second step of Example 1, except that the starting raw material was changed to 3,3'-(2,5-dimethoxy-1,4-phenylene)bis(7-decyl-2-methoxynaphthalene) (3.50 g, 4.79 mmol), and that 21.1 ml (21.1 mmol) of boron tribromide (1.0 M dichloromethane solution) was used. The yield was 81%. The physical property values of the obtained compound are shown as follows.

Melting point: 269.5-270.5° C., $^1$H NMR (600 MHz, acetone-d$_6$): δ0.92 (t, J=7.2 Hz, 6H, CH$_3$), 1.26-1.42 (m, 28H, (CH$_2$)$_7$), 1.76 (quin, J=7.2 Hz, 4H, ArCH$_2$CH$_2$), 2.80 (t, J=7.2 Hz, 4H, ArCH$_2$), 2.88 (brs, 4H, OH), 7.10 (s, 2H, ArH), 7.27 (d, J=8.4 Hz, 2H, ArH), 7.36 (s, 2H, ArH), 7.58 (s, 2H, ArH), 7.83 (d, J=8.4 Hz, 2H, ArH), 7.88 (s, 2H, ArH). $^{13}$C NMR (150 MHz, THF-d$_8$): δ15.04, 24.16, 30.87, 30.90, 31.15, 31.21 (two carbons), 33.01, 33.46, 37.63, 111.75, 120.87, 125.70, 126.07, 128.22, 129.03, 129.06, 129.56, 131.80, 136.28, 141.79, 149.28, 154.54. TOF HRMS (APCI+): Calcd for C46H59O4 [M+H] 675.4413, found, 675.4404. Anal. Calcd for C46H58O4: C, 81.86; H, 8.66. Found C, 81.66; H, 8.63.

(Third Step)

Synthesis of 3,11-didecyldinaphtho[2,3-d:2',3'-d']benzo[1,2-b:4,5-b']difuran

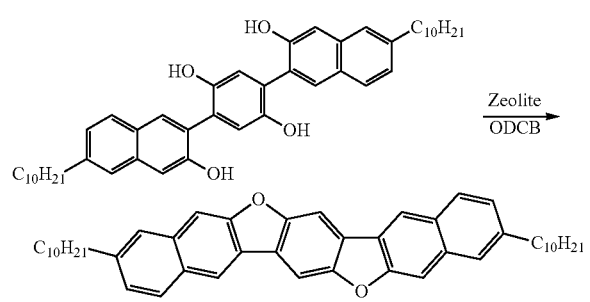

To 2,5-bis(6-decyl-3-hydroxynaphthalene-2-yl)benzene-1,4-diol (820 mg, 1.21 mmol), as its suspension in o-dichlorobenzene (24 mL), zeolite (329 mg) was added, and the mixture was stirred at 160° C. for 16 hours. The solution was filtered without cooling to remove the zeolite catalyst, then methanol was added thereto, and the obtained product material in light-yellow colored solid was isolated by vacuum filtration. The obtained amount was 579 mg, at 78% of yield.

Melting point: 350° C. or more. $^1$H NMR (600 MHz, CDCl$_2$CDCl$_2$ at 100° C.) δ 0.89 (t, J=6.6 Hz, 6H, CH$_3$), 1.25-1.44 (m, 28H, (CH$_2$)$_7$), 1.78 (quin, J=7.2 Hz, 4H, ArCH$_2$CH$_2$), 2.83 (t, J=7.2 Hz, 4H, ArCH$_2$), 7.34 (d, J=8.4 Hz, 2H, ArH), 7.72 (s, 2H, ArH), 7.86 (s, 2H, ArH), 7.95 (d, J=8.4 Hz, 2H, ArH), 8.12 (s, 2H, ArH), 8.40 (s, 2H, ArH). TOF HRMS (APCI+): Calcd for C$_{46}$H$_{55}$O$_2$ [M+H] 639.4202, found, 639.4197. Anal. Calcd for C$_{46}$H$_{54}$O$_2$: C, 86.47; H, 8.52. Found C, 86.63; H, 8.14.

Example 4

Synthesis of 3,11-didecyldinaphtho[2,3-d:2',3'-d']benzo[1,2-b:4,5-b']dithiophene (First Step)

Synthesis of O,O'-(2,5-bis(6-decyl-3-((dimethylcarbamoylthioyl)oxy)naphthalene-2-yl)-1,4-phenylene)bis(dimethylcarbamothioate)

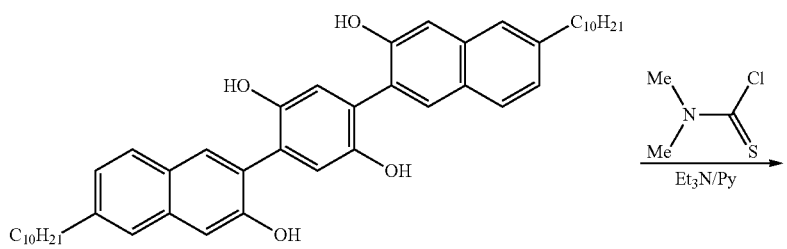

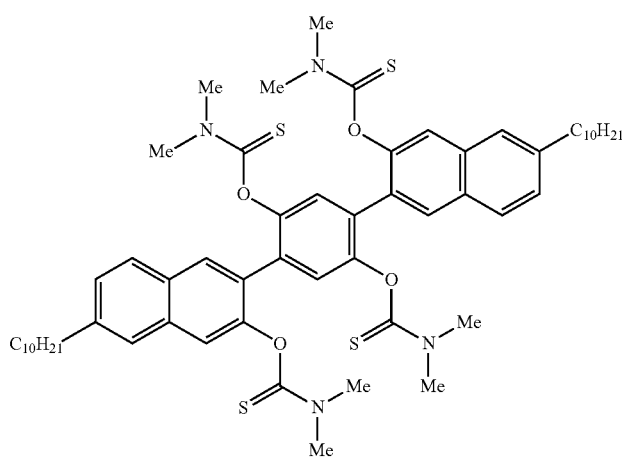

The titled compound in white solid (2.63 g, 0.570 mmol) was obtained in accordance with the first step of Example 2, except that the starting raw material was changed to 2,5-bis(6-decyl-3-hydroxynaphthalene-2-yl)benzene-1,4-diol (2.70 g, 4.00 mmol) obtained in the second step in Example 3, and that 4.27 ml of triethylamine, 16.7 ml of pyridine, and 3.96 g (32.0 mmol) of N,N-dimethylcarbamoylthiochloride were used. The yield was 48%. The physical property values of the obtained compound are shown as follows.

Melting point: 229.5-230.5° C. $^1$H NMR (600 MHz, CDCl$_3$): δ0.89 (t, J=7.2 Hz, 6H, CH$_3$), 1.26-1.38 (m, 28H, (CH$_2$)$_7$), 1.71 (quin, J=7.8 Hz, 4H, ArCH$_2$CH$_2$), 2.77 (t, J=7.8 Hz, 4H, ArCH$_2$), 2.97 (s, 6H, NH$_3$), 3.14 (s, 6H, NH$_3$), 3.23 (s, 6H, NH$_3$), 3.38 (s, 6H, NH$_3$), 7.31 (d, J=8.4 Hz, 2H, ArH), 7.37 (s, 2H, ArH), 7.57 (s, 2H, ArH), 7.60 (s, 2H, ArH), 7.74 (d, J=8.4 Hz, 2H, ArH), 7.93 (s, 2H, ArH). $^{13}$C NMR (150 MHz, CDCl$_3$): δ14.31, 22.85, 29.51, 29.60, 29.72, 29.77, 29.80, 31.48, 32.07, 36.34, 38.60, 39.32, 43.14, 43.55, 121.10, 126.11, 126.67, 127.70, 127.79, 128.18, 129.66, 130.64, 131.26, 133.48, 141.47, 148.71, 149.54, 187.04, 187.22. TOF HRMS (APCI+): Calcd for C$_{58}$H$_{79}$N$_4$O$_4$S$_4$ [M+H] 1023.4984, found, 1023.4986. Anal. Calcd for C$_{58}$H$_{78}$N$_4$O$_4$S$_4$: C, 68.06; H, 7.68; N, 5.47. Found C, 68.13; H, 7.75; N, 5.31.

(Second Step)

Synthesis of 3,11-didecyldinaphtho[2,3-d:2',3'-d']benzo[1,2-b:4,5-b']dithiophene

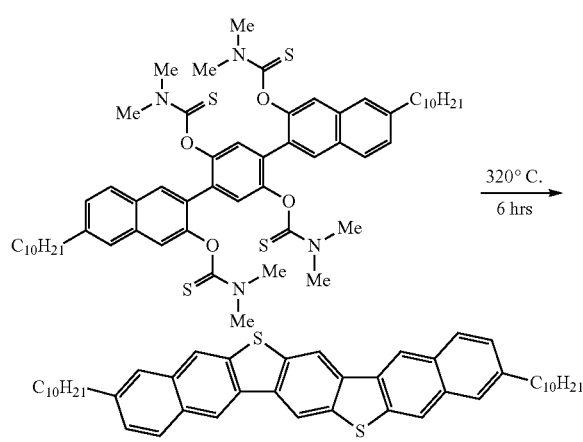

The titled compound in yellow solid (530 mg, 0.790 mmol) was obtained in accordance with the second step of Example 2, except that the starting raw material was changed to O,O'-(2,5-bis(6-decyl-3-((dimethylcarbamoylthioyl)oxy)naphthalene-2-yl)-1,4-phenylene)bis(dimethylcarbamothioate) (1.64 g, 1.60 mmol). The yield was 48%. The physical property values of the obtained compound are shown as follows.

Melting point: 263-264° C. $^1$H NMR (600 MHz, CDCl$_2$CDCl$_2$, 100° C.): δ0.89 (t, J=6.6 Hz, 6H, CH$_3$), 1.26-1.44 (m, 28H, (CH$_2$)$_7$), 1.77 (quin, J=7.2 Hz, 4H, ArCH$_2$CH$_2$), 2.83 (t, J=7.2 Hz, 4H, ArCH$_2$), 7.37 (d, J=8.4 Hz, 2H, ArH), 7.66 (s, 2H, ArH), 7.94 (d, J=8.4 Hz, 2H, ArH), 8.19 (s, 2H, ArH), 8.59 (s, 4H, ArH). $^{13}$C NMR (150 MHz, CDCl$_2$CDCl$_2$, 100° C.): δ13.99, 22.61, 29.25, 29.42, 29.50, 29.59 (two carbons), 31.04, 31.88, 36.26, 115.60, 120.01, 120.21, 125.24, 127.30, 128.31, 129.72, 133.31, 133.69, 135.53, 137.20, 138.28, 141.32. TOF HRMS (APCI+): Calcd for C$_{46}$H$_{55}$S$_2$ [M+H] 671.3745, found, 671.3745. Anal. Calcd for C$_{46}$H$_{54}$S$_2$: C, 82.33; H, 8.11. Found: C, 82.34; H, 8.12.

Example 5

Synthesis of 3,11-dihexyldinaphtho[2,3-d:2',3'-d']benzo[1,2-b:4,5-b']dithiophene (First Step)

Synthesis of 3,3'-(2,5-dimethoxy-1,4-phenylene)bis(7-hexyl-2-methoxynaphthalene)

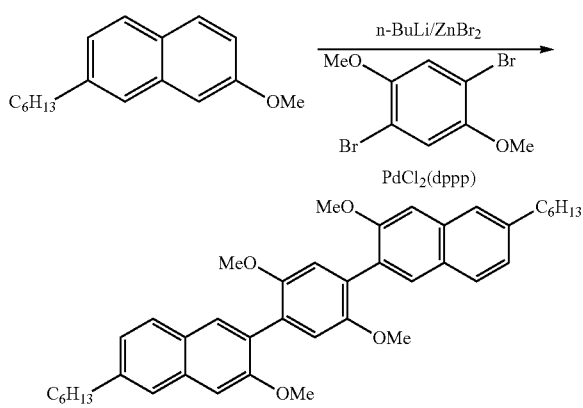

The titled compound in white solid (4.32 g, 7.00 mmol) was obtained in accordance with the first step of Example 3, except that the starting raw material was changed to 2-hexyl-7-methoxynaphthalene (4.85 g, 20.0 mmol), and that 13.6 ml (22.0 mmol) of n-butyllithium (1.62 M hexane solution), 22.0 ml (22.0 mmol) of zinc bromide (1.0 M THF solution), 2.50 g (8.41 mmol) of 1,4-dibromo-2,5-dimethoxybenzene, and 250 mg (0.42 mmol) of PdCl$_2$(dppp) were used. The yield was 83%. The physical property values of the obtained compound are shown as follows.

Melting point: 165.2-166.0° C. $^1$H NMR (600 MHz, CDCl$_3$): δ0.90 (t, J=6.6 Hz, 6H, CH$_3$), 1.31-1.38 (m, 12H, (CH$_2$)$_3$), 1.71 (quin, J=7.8 Hz, 4H, ArCH$_2$CH$_2$), 2.77 (t, J=7.8 Hz, 4H, ArCH$_2$), 3.74 (s, 6H, OCH$_3$), 3.94 (s, 6H, OCH$_3$), 6.98 (s, 2H, ArH), 7.19 (s, 2H, ArH), 7.20 (d, J=8.4 Hz, 2H, ArH), 7.56 (s, 2H, ArH), 7.71 (d, J=8.4 Hz, 2H, ArH), 7.75 (s, 2H, ArH). $^{13}$C NMR (150 MHz, CDCl$_3$): δ14.32, 22.81, 29.15, 31.58, 31.96, 36.37, 55.84, 56.75, 105.26, 115.43, 125.19, 125.46, 127.22, 127.65, 127.77, 128.89, 130.38, 134.51, 141.04, 151.35, 156.09. TOF HRMS (APCI+): Calcd for C42H51O4 [M+H] 619.3787, found, 619.3788.

(Second Step)

Synthesis of 2,5-bis(6-hexyl-3-hydroxynaphthalene-2-yl)benzene-1,4-diol

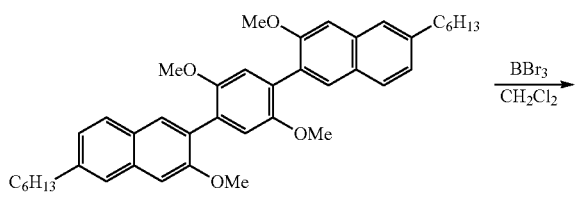

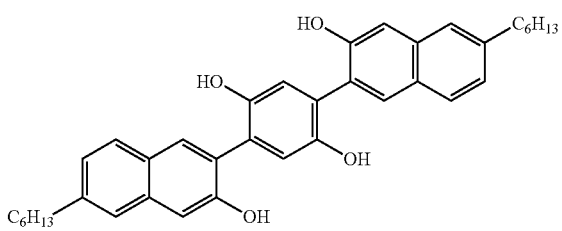

The titled compound in white solid (2.46 g, 4.38 mmol) was obtained in accordance with the second step of Example 3, except that the starting raw material was changed to 3,3'-(2,5-dimethoxy-1,4-phenylene)bis(7-hexyl-2-methoxynaphthalene) (3.09 g, 5.00 mmol), and that 22.0 ml (22.0 mmol) of boron tribromide (1.0 M dichloromethane solution) was used. The yield was 88%. The physical property values of the obtained compound are shown as follows.

Melting point: 250.7-251.5° C. $^1$H NMR (600 MHz, acetone-$d_6$): δ0.93 (t, J=7.2 Hz, 6H, CH$_3$), 1.35-1.45 (m, 12H, (CH$_2$)$_3$), 1.76 (quin, J=7.2 Hz, 4H, ArCH$_2$CH$_2$), 2.81 (t, J=7.2 Hz, 4H, ArCH$_2$), 2.88 (brs, 4H, OH), 7.10 (s, 2H, ArH), 7.27 (d, J=8.4 Hz, 2H, ArH), 7.36 (s, 2H, ArH), 7.58 (s, 2H, ArH), 7.83 (d, J=8.4 Hz, 2H, ArH), 7.88 (s, 2H, ArH). TOF HRMS (APCI+): Calcd for C$_{38}$H$_{43}$O$_4$ [M+H] 563.3161, found, 563.3154. Anal. Calcd for C$_{38}$H$_{42}$O$_4$: C, 81.10; H, 7.52. Found C, 80.83; H, 7.64.

(Third Step)

Synthesis of O,O'-(2,5-bis(6-hexyl-3-((dimethylcarbamoylthioyl)oxy)naphthalene-2-yl)-1,4-phenylene) bis(dimethylcarbamothioate)

The titled compound in white solid (2.27 g, 2.36 mmol) was obtained in accordance with the first step of Example 2, except that the starting raw material was changed to 2,5-bis(6-hexyl-3-hydroxynaphthalene-2-yl)benzene-1,4-diol (2.25 g, 4.00 mmol) obtained in the second step of this example, and that 4.27 ml of triethylamine, 1.67 ml of pyridine, and 3.96 g (32.0 mmol) of N,N-dimethylcarbamoylthiochloride were used. The yield was 59%. The physical property values of the obtained compound are shown as follows.

Melting point: 244.0-245.0° C. $^1$H NMR (600 MHz, CDCl$_3$): δ0.90 (t, J=7.2 Hz, 6H, CH$_3$), 1.31-1.39 (m, 12H, (CH$_2$)$_3$), 1.71 (quin, J=7.8 Hz, 4H, ArCH$_2$CH$_2$), 2.77 (t, J=7.8 Hz, 4H, ArCH$_2$), 2.97 (s, 6H, NH$_3$), 3.14 (s, 6H, NH$_3$), 3.23 (s, 6H, NH$_3$), 3.38 (s, 6H, NH$_3$), 7.31 (d, J=8.4 Hz, 2H, ArH), 7.37 (s, 2H, ArH), 7.57 (s, 2H, ArH), 7.60 (s, 2H, ArH), 7.74 (d, J=8.4 Hz, 2H, ArH), 7.93 (s, 2H, ArH). $^{13}$C NMR (150 MHz, CDCl$_3$): δ14.29, 22.78, 29.26, 31.42, 31.92, 36.33, 38.59, 39.32, 43.14, 43.54, 121.10, 126.11, 126.67, 127.70, 127.80, 128.18, 129.66, 130.64, 131.26, 133.48, 141.46, 148.72, 149.54, 187.05, 187.22. TOF HRMS (APCI+): Calcd for C$_{50}$H$_{63}$N$_4$O$_4$S$_4$ [M+H] 911.3732, found, 911.3740. Anal. Calcd for C$_{50}$H$_{62}$N$_4$O$_4$S$_4$: C, 65.90; H, 6.86; N, 6.15. Found C, 65.65; H, 6.79; N, 6.11.

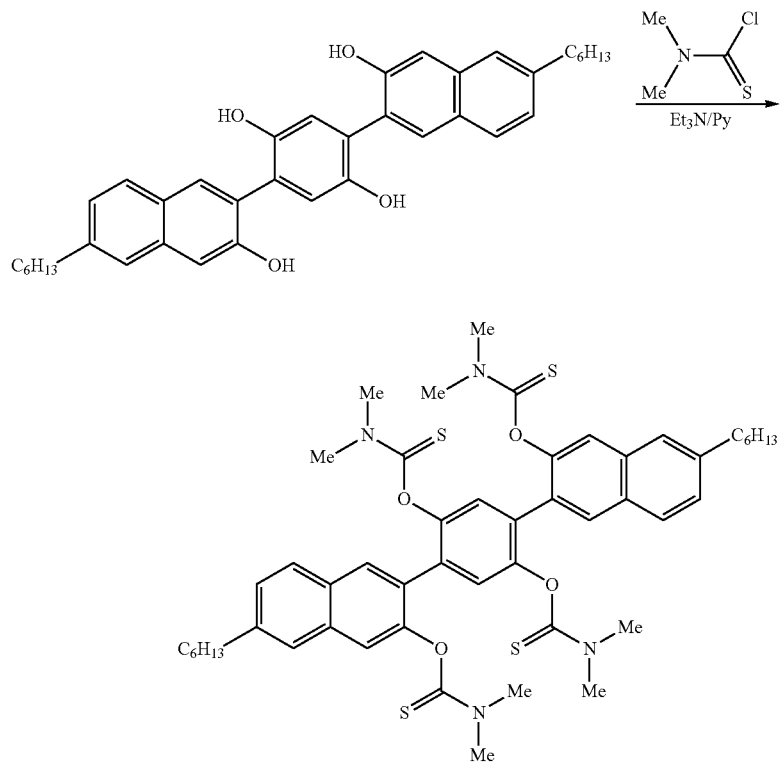

(Fourth Step)

Synthesis of 3,11-dihexyldinaphtho[2,3-d:2',3'-d']benzo[1,2-b:4,5-b']dithiophene

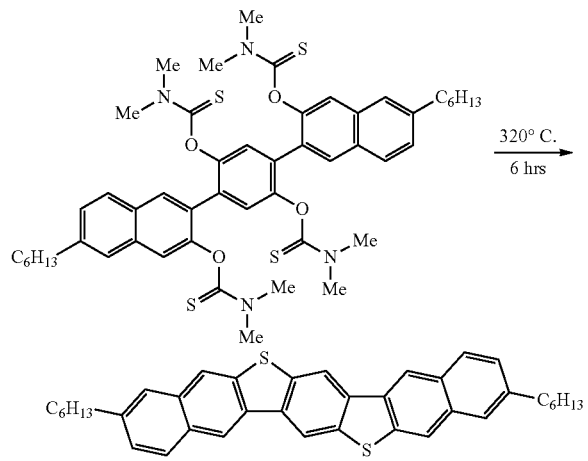

The titled compound in yellow solid (615 mg, 1.10 mmol) was obtained in accordance with the second step of Example 2, except that the starting raw material was changed to O,O'-(2,5-bis(6-hexyl-3-((dimethylcarbamoylthioyl)oxy)naphthalene-2-yl)-1,4-phenylene)bis(dimethylcarbamothioate) (1.82 g, 2.00 mmol). The yield was 48%. The physical property values of the obtained compound are shown as follows.

Melting point: >300° C. $^1$H NMR (600 MHz, CDCl$_2$CDCl$_2$, 100° C.): δ0.89 (t, J=6.6 Hz, 6H, CH$_3$), 1.26-1.44 (m, 12H, (CH$_2$)$_3$), 1.77 (quin, J=7.2 Hz, 4H, ArCH$_2$CH$_2$), 2.83 (t, J=7.2 Hz, 4H, ArCH$_2$), 7.37 (d, J=8.4 Hz, 2H, ArH), 7.66 (s, 2H, ArH), 7.94 (d, J=8.4 Hz, 2H, ArH), 8.19 (s, 2H, ArH), 8.60 (s, 4H, ArH). TOF HRMS (APCI+): Calcd for C$_{38}$H$_{39}$S$_2$ [M+H] 559.2493, found, 559.2485. Anal. Calcd for C$_{38}$H$_{38}$S$_2$: C, 81.67; H, 6.85. Found: C, 81.77; H, 6.94.

Example 6

Synthesis of 3,12-didecyldinaphtho[2,3-d:2',3'-d']naphtho[1,2-b:6,7-b']difuran (First Step)

Synthesis of 6,6''-didecyl-3,3',3'',7'-tetramethoxy-2,2':6',2''-ternaphthalene

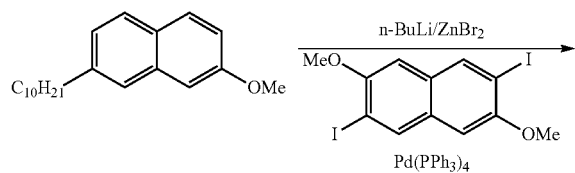

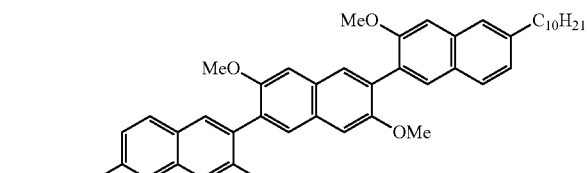

To 2-decyl-7-methoxynaphthalene (14.7 g, 49.3 mmol), as its THF (192 ml) solution, 34.1 ml (54.2 mmol) of n-butyllithium (1.59M hexane solution) was added at 0° C., and the mixture was stirred at 0° C. for 2 hours. 54.2 ml (54.2 mmol) of zinc bromide (1.0 M THF solution) was added thereto, then the temperature was put back at room temperature, and the solution was stirred for 1 hour. To the obtained light yellow colored solution, 2,6-diiode-3,7-dimethoxynaphthalene (9.00 g, 20.5 mmol) and Pd(PPh$_3$)$_4$ (1.15 g, 1.00 mmol) were added, and the solution was kept stirred at room temperature for 16 hours. Water was added to the reaction solution, the reaction solution was extracted with chloroform, then washed with saturated saline solution, and dried with anhydrous magnesium sulfate. The reaction solution was filtered to remove the drying agent, and then concentrated under reduced pressure to remain approximately 40 ml of the reaction solution, acetone and dichloromethane were added thereto for re-precipitation, and the resulted precipitate was filtered to obtain the titled compound in white solid (10.5 g, 13.4 mmol). The solution filtered off was concentrated under reduced pressure, and the remained residue was purified with silica gel column chromatography (hexane:ethyl acetate=80:20 (volume ratio)), to collect the titled compound (4.28 g, 5.48 mmol). The total yield summing up both was 92%. The physical property values of the obtained compound are shown as follows.

Melting point: 142.9-143.6° C. $^1$H NMR (600 MHz, CDCl$_3$) δ0.90 (t, J=6.6 Hz, 6H, CH$_3$), 1.26-1.39 (m, 28H, (CH$_2$)$_7$), 1.73 (quin, J=7.2 Hz, 4H, ArCH$_2$CH$_2$), 2.78 (t, J=7.2 Hz, 4H, ArCH$_2$), 3.85 (s, 6H, OCH$_3$), 3.89 (s, 6H, OCH$_3$), 7.18 (s, 2H, ArH), 7.21 (s, 2H, ArH), 7.22 (d, J=8.4 Hz, 2H, ArH), 7.58 (s, 2H, ArH), 7.71 (s, 2H, ArH), 7.72 (d, J=8.4 Hz, 2H, ArH), 7.73 (s, 2H, ArH). $^{13}$C NMR (150 MHz, CDCl$_3$): δ14.32, 22.88, 29.52 (two carbons), 29.75, 29.80, 29.82, 31.65, 32.09, 36.38, 55.81, 55.93, 105.10, 105.79, 125.22, 125.42, 127.25, 127.67, 129.08, 129.35 (two carbons), 130.05, 130.30, 134.64, 141.03, 155.05, 156.47. TOF HRMS (APCI+): Calcd for C$_{54}$H$_{69}$O$_4$ [M+H] 781.5196, found, 781.5200. Anal. Calcd for C$_{54}$H$_{68}$O$_4$: C, 83.03; H, 8.77. Found C, 82.78; H, 8.79.

45

(Second Step)

Synthesis of 6,6"-didecyl[2,2':6',2"-ternaphthalene]-3,3',3",7'-tetraol

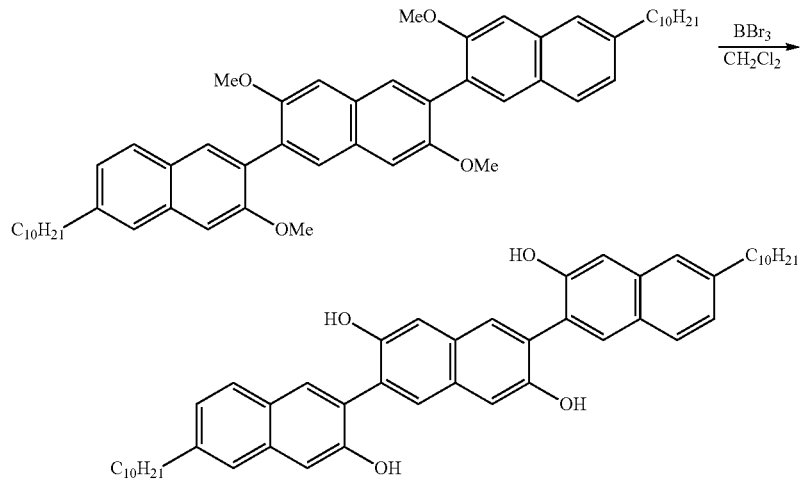

The titled compound in white solid was obtained in accordance with the second step of Example 1, except that the starting raw material was changed to 6,6"-didecyl-3,3',3",7'-tetramethoxy-2,2':6',2"-ternaphthalene (1.67 g, 5.00 mmol), and that 11.0 ml (11.0 mmol) of boron tribromide (1.0M dichloromethane solution) was used. The yield was 81%. The physical property values of the obtained compound are shown as follows.

Melting point: 269.5-270.5° C. $^1$H NMR (600 MHz, acetone-$d_6$): δ0.92 (t, J=7.2 Hz, 6H, $CH_3$), 1.26-1.42 (m, 28H, $(CH_2)_7$), 1.76 (quin, J=7.2 Hz, 4H, $ArCH_2CH_2$), 2.81 (t, J=7.2 Hz, 4H, $ArCH_2$), 2.85 (brs, 4H, OH), 7.26 (d, J=8.4 Hz, 2H, ArH), 7.36 (s, 2H, ArH), 7.41 (s, 2H, ArH), 7.58 (s, 2H, ArH), 7.79 (s, 2H, ArH), 7.83 (d, J=8.4 Hz, 2H, ArH), 7.90 (s, 2H, ArH). $^{13}$C NMR (150 MHz, THF-$d_8$): δ15.03, 23.16, 30.90 (two carbons), 31.14, 31.21 (two carbons), 32.99, 33.46, 37.65, 111.33, 111.63, 125.71, 125.95, 128.94, 128.99, 130.10, 130.36, 131.00, 131.23, 132.05, 136.44, 141.75, 152.88, 154.96. HRMS (APCI+): Calcd for $C_{50}H_{61}O_4$ [M+H] 725.4570, found, 725.4561.

46

(Third Step)

Synthesis of 3,12-didecyldinaphtho[2,3-d:2',3'-d']naphtho[1,2-b:6,7-b']difuran

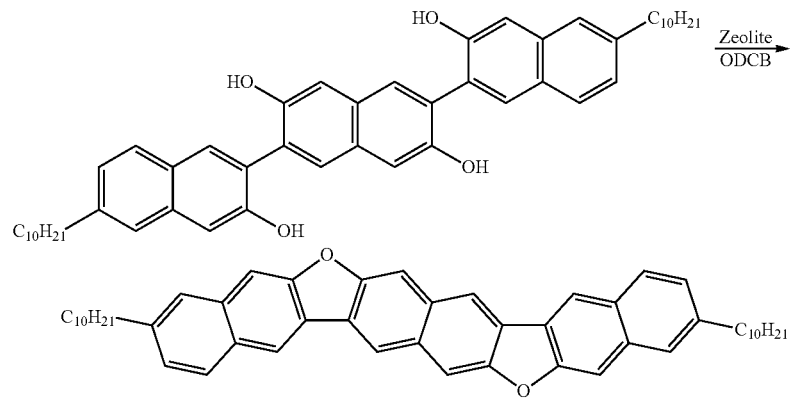

The titled compound in yellow solid (666 mg, 0.967 mmol) was obtained in accordance with the third step of Example 3, except that the starting raw material was changed to 6,6"-didecyl-[2,2':6',2"-ternaphthalene]-3,3',3",7'-tetraol (1.02 g, 1.40 mmol). The yield was 69%. The physical property values of the obtained compound are shown as follows.

Melting point: 300° C. or more. $^1$H NMR (600 MHz, $CD_2Cl_2CD_2Cl_2$ at 120° C.) δ0.90 (t, J=6.6 Hz, 6H, $CH_3$), 1.25-1.44 (m, 28H, $(CH_2)_7$), 1.79 (quin, J=7.2 Hz, 4H, $ArCH_2CH_2$), 2.84 (t, J=7.2 Hz, 4H, $ArCH_2$), 7.34 (d, J=8.4 Hz, 2H, ArH), 7.72 (s, 2H, ArH), 7.81 (s, 2H, ArH), 7.95 (d, J=8.4 Hz, 2H, ArH), 8.05 (s, 2H, ArH), 8.48 (s, 2H, ArH), 8.57 (s, 2H, ArH). HRMS (APCI+): Calcd for $C_{50}H_{57}O_2$ [M+H] 689.4359, found, 689.4346.

Example 7

Synthesis of 3,12-didecyldinaphtho[2,3-d:2',3'-d']naphtho[1,2-b:6,7-b']dithiophene (First Step)

Synthesis of O,O',O'',O'''-(6,6''-didecyl-[2,2':6',2''-ternaphthalene]-3,3',3'',7'-tetrayl)tetrakis(dimethylcarbamothioate)

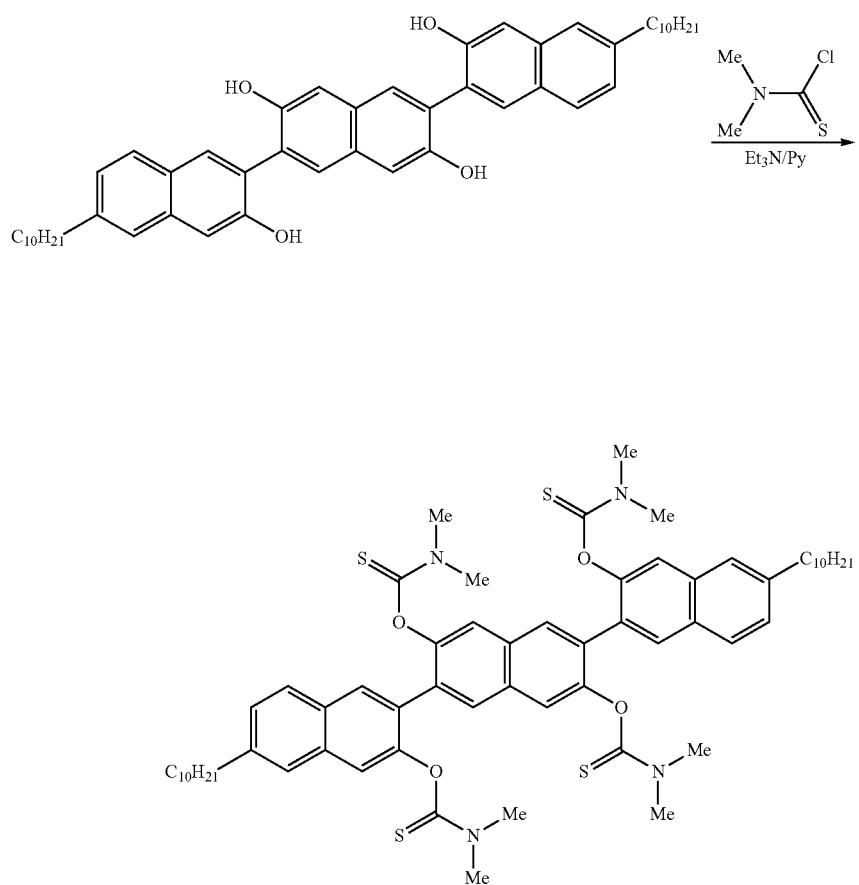

To a suspension of 6,6''-didecyl-[2,2':6',2''-ternaphthalene]-3,3',3'',7'-tetraol (870 mg, 1.20 mmol) and THF (9.6 ml), triethylamine (1.28 ml), pyridine (0.50 ml), N,N-dimethylcarbamoylthiochloride (1.19 g, 9.60 mmol) were added. This solution was kept being reacted at 65° C. for 72 hours, and then concentrated to remove the solvent etc. under reduced pressure. The residue was purified with aluminum column (hexane:ethyl acetate=95:5 to 80:20 (volume ratio)) to obtain the titled compound in white solid (612 mg, 0.570 mmol). The yield was 48%. The physical property values of the obtained compound are shown as follows.

Melting point: 193.8-194.5° C. $^1$H NMR (600 MHz, CDCl$_3$) δ0.89 (t, J=7.2 Hz, 6H, CH$_3$), 1.26-1.40 (m, 28H, (CH$_2$)$_7$), 1.74 (quin, J=7.8 Hz, 4H, ArCH$_2$CH$_2$), 2.79 (t, J=7.8 Hz, 4H, ArCH$_2$), 3.05 (s, 6H, NCH$_3$), 3.06 (s, 6H, NCH$_3$), 3.19 (s, 6H, NCH$_3$), 3.24 (s, 6H, NCH$_3$), 7.34 (d, J=7.8 Hz, 2H, ArH), 7.59 (s, 2H, ArH), 7.63 (s, 4H, ArH), 7.78 (d, J=7.8 Hz, 2H, ArH), 7.97 (s, 2H, ArH) 7.98 (s, 2H, ArH). $^{13}$C NMR (150 MHz, CDCl$_3$): δ14.31, 22.86, 29.51, 29.60, 29.73, 29.78, 29.80, 31.52, 32.07, 36.35, 38.63, 38.66, 43.26, 43.33, 120.79, 121.40, 126.13, 127.80, 127.95, 129.01, 129.88, 130.84, 130.92, 131.00, 131.11, 133.54, 141.58, 149.84, 150.05, 187.40 (two carbons). TOF HRMS (APCI+): Calcd for C$_{62}$H$_{81}$N$_4$O$_4$S$_4$ [M+H] 1073.5141, found, 1073.5153. Anal. Calcd for C$_{62}$H$_{80}$N$_4$O$_4$S$_4$: C, 69.36; H, 7.51; N, 5.22. Found C, 69.07; H, 7.49; N, 5.27.

(Second Step)

Synthesis of 3,12-didecyldinaphtho[2,3-d:2',3'-d']naphtho[1,2-b:6,7-b']dithiophene

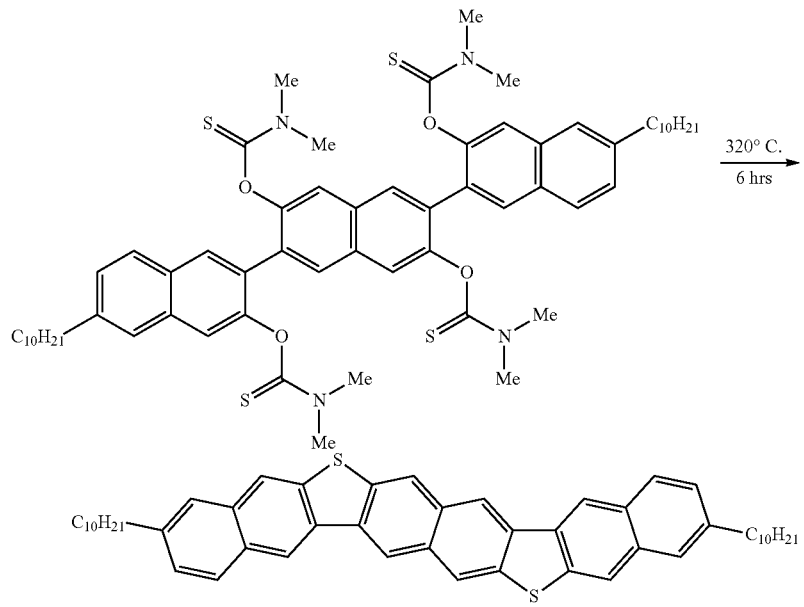

291 mg (0.27 mmol) of O,O',O'',O'''-(6,6''-didecyl-[2,2':6',2''-ternaphthalene]-3,3',3'',7'-tetrayl)tetrakis(dimethylcarbamothioate) was sealed in a Pyrex (registered trademark) tube, and heated at 320° C. for 6 hours. The temperature was put back at room temperature, the tube was unsealed, the resulted inside material was put into ultrasonic cleaning process in chloroform, and then filtered and thermally re-crystallized in 1,1,2,2-tetrachloroethane to obtain the titled compound in yellow solid (106 mg, 0.147 mmol). The yield was 54%. The physical property values of the obtained compound are shown as follows.

Melting point: 300° C. or more. $^1$H NMR (600 MHz, CDCl$_2$CDCl$_2$, 100° C.): δ0.89 (t, J=7.2 Hz, 6H, CH$_3$), 1.26-1.43 (m, 28H, (CH$_2$)$_7$), 1.77 (quin, J=7.2 Hz, 4H, ArCH$_2$CH$_2$), 2.82 (t, J=7.2 Hz, 4H, ArCH$_2$), 7.38 (d, J=8.4 Hz, 2H, ArH), 7.65 (s, 2H, ArH), 7.96 (d, J=8.4 Hz, 2H, ArH), 8.13 (s, 2H, ArH), 8.37 (s, 2H, ArH), 8.65 (s, 2H, ArH), 8.68 (s, 2H, ArH). TOF HRMS (APCI+): Calcd for C$_{50}$H$_{57}$S$_2$ [M+H] 721.3902, found, 721.3890. Anal. Calcd for C$_{50}$H$_{56}$S$_2$: C, 83.28; H, 7.83. Found: C, 83.52; H, 7.55.

Example 8

Synthesis of 3,12-dihexyldinaphtho[2,3-d:2',3'-d']naphtho[1,2-b:6,7-b']dithiophene (First Step)

Synthesis of 6,6''-dihexyl-3,3',3'',7'-tetramethoxy-2,2':6',2''-ternaphthalene

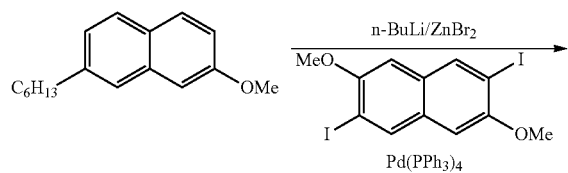

-continued

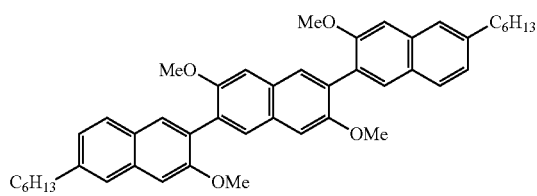

The titled compound in white solid (5.04 g, 7.53 mmol) was used in accordance with the first step of Example 6, except that the starting raw material was changed to 2-hexyl-7-methoxynaphthalene (4.85 g, 20.0 mmol), and that 13.6 ml (22.0 mmol) of n-butyllithium (1.62M hexane solution), 22.0 ml (22.0 mmol) of zinc bromide (1.0 M THF solution), 3.70 g (8.40 mmol) of 2,6-diiode-3,7-dimethoxynaphthalene, and 490 mg (0.42 mmol) of Pd(PPh$_3$)$_4$ were used. The yield was 90%. The physical property values of the obtained compound are shown as follows.

Melting point: 210.7-211.5° C. $^1$H NMR (600 MHz, CDCl$_3$) δ0.91 (t, J=6.6 Hz, 6H, CH$_3$), 1.32-1.39 (m, 12H, (CH$_2$)$_3$), 1.72 (quin, J=7.8 Hz, 4H, ArCH$_2$CH$_2$), 2.78 (t, J=7.8 Hz, 4H, ArCH$_2$), 3.84 (s, 6H, OCH$_3$), 3.88 (s, 6H, OCH$_3$), 7.18 (s, 2H, ArH), 7.20 (s, 2H, ArH), 7.21 (d, J=8.4 Hz, 2H, ArH), 7.57 (s, 2H, ArH), 7.70 (s, 2H, ArH), 7.71 (d, J=8.4 Hz, 2H, ArH), 7.72 (s, 2H, ArH). $^{13}$C NMR (150 MHz, CDCl$_3$): δ14.32, 22.81, 29.19, 31.60, 31.97, 36.38, 55.81, 55.92, 105.11, 105.80, 125.21, 125.41, 127.26, 127.67, 129.09, 129.33, 129.35, 130.05, 130.30, 134.64, 141.02, 155.05, 156.47. TOF HRMS (APCI+): Calcd for C$_{46}$H$_{53}$O$_4$ [M+H] 669.3944, found, 669.3944. Anal. Calcd for C$_{46}$H$_{52}$O$_4$: C, 82.60; H, 7.84. Found C, 82.24; H, 7.80.

(Second Step)

Synthesis of 6,6"-dihexyl-[2,2':6',2"-ternaphthalene]-3,3',3",7'-tetraol

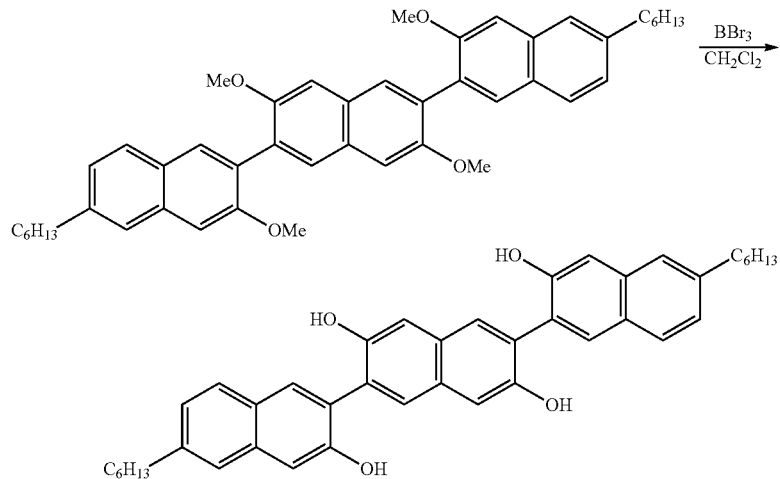

The titled compound in white solid was obtained in accordance with the second step of Example 1, except that the starting raw material was changed to 6,6"-dihexyl-3,3',3",7'-tetramethoxy-2,2':6',2"-ternaphthalene (3.34 g, 5.00 mmol), and that 22.0 ml (22.0 mmol) of boron tribromide (1.0M dichloromethane solution) was used. The yield was 79%. The physical property values of the obtained compound are shown as follows.

Melting point: 300° C. or more. $^1$H NMR (600 MHz, acetone-d$_6$): δ0.94 (t, J=7.2 Hz, 6H, CH$_3$), 1.36-1.45 (m, 12H, (CH$_2$)$_3$), 1.77 (quin, J=7.2 Hz, 4H, ArCH$_2$CH$_2$), 2.81 (t, J=7.2 Hz, 4H, ArCH$_2$), 2.85 (brs, 4H, OH), 7.27 (d, J=8.4 Hz, 2H, ArH), 7.36 (s, 2H, ArH), 7.41 (s, 2H, ArH), 7.59 (s, 2H, ArH), 7.79 (s, 2H, ArH), 7.83 (d, J=8.4 Hz, 2H, ArH), 7.89 (s, 2H, ArH). HRMS (APCI+): Calcd for C$_{42}$H$_{45}$O$_4$ [M+H] 613.3318, found, 613.3305.

(Third Step)

Synthesis of O,O',O",O'"-(6,6"-dihexyl-[2,2':6',2"-ternaphthalene]-3,3',3",7'-tetrayl)tetrakis(dimethylcarbamothioate)

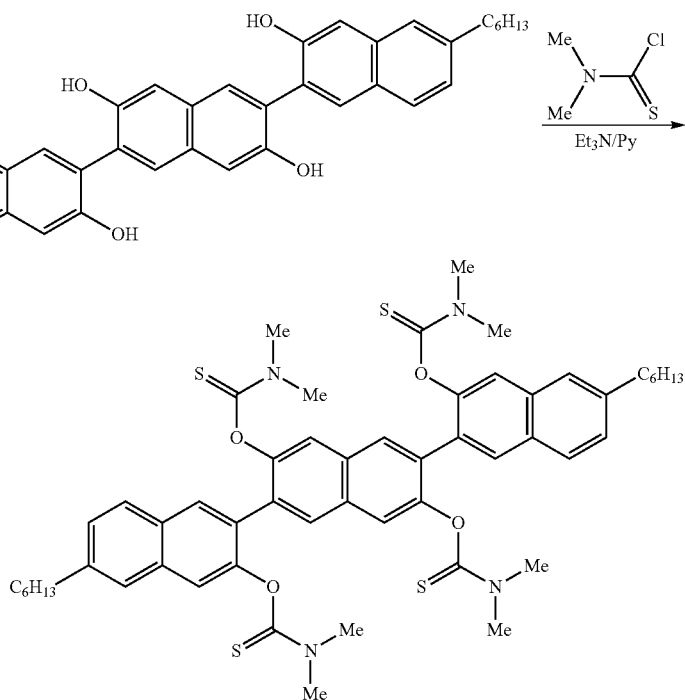

To a suspension of 6,6"-dihexyl-[2,2':6',2"-ternaphthalene]-3,3',3",7'-tetraol (1.84 g, 3.00 mmol) and THF (12.0 ml), triethylamine (3.20 ml), pyridine (1.30 ml), N,N-dimethylcarbamoylthiochloride (2.97 g, 24.0 mmol) were added. This solution was kept being reacted at 65° C. for 18 hours, and then concentrated to remove the solvent etc. under reduced pressure. The residue was purified with aluminum column (hexane:ethyl acetate=95:5 to 80:20 (volume ratio)) to obtain the titled compound in white solid (1.49 g, 15.5 mmol). The yield was 52%. The physical property values of the obtained compound are shown as follows.

Melting point: 256.3-257.3° C. $^1$H NMR (600 MHz, CDCl$_3$) δ0.91 (t, J=7.2 Hz, 6H, CH$_3$), 1.33-1.41 (m, 12H, (CH$_2$)$_3$), 1.73 (quin, J=7.2 Hz, 4H, ArCH$_2$CH$_2$), 2.79 (t, J=7.2 Hz, 4H, ArCH$_2$), 3.03 (s, 6H, NCH$_3$), 3.06 (s, 6H, NCH$_3$), 3.19 (s, 6H, NCH$_3$), 3.23 (s, 6H, NCH$_3$), 7.34 (d, J=7.8 Hz, 2H, ArH), 7.59 (s, 2H, ArH), 7.63 (s, 4H, ArH), 7.78 (d, J=7.8 Hz, 2H, ArH), 7.96 (s, 2H, ArH) 7.98 (s, 2H, ArH). $^{13}$C NMR (150 MHz, CDCl$_3$): δ14.29, 22.79, 29.26, 31.46, 31.92, 36.34, 38.62, 38.66, 43.25, 43.33, 120.79, 121.39, 126.13, 127.80, 127.95, 129.01, 129.87, 130.84, 130.91, 131.00, 131.11, 133.54, 141.58, 149.85, 150.05, 187.39 (two carbons). TOF HRMS (APCI+): Calcd for C54H65N4O4S4 [M+H] 961.3889, found, 961.3890.

Fourth Step

Synthesis of 3,12-dihexyldinaphtho[2,3-d:2',3'-d']naphtho[1,2-b:6,7-b']dithiophene

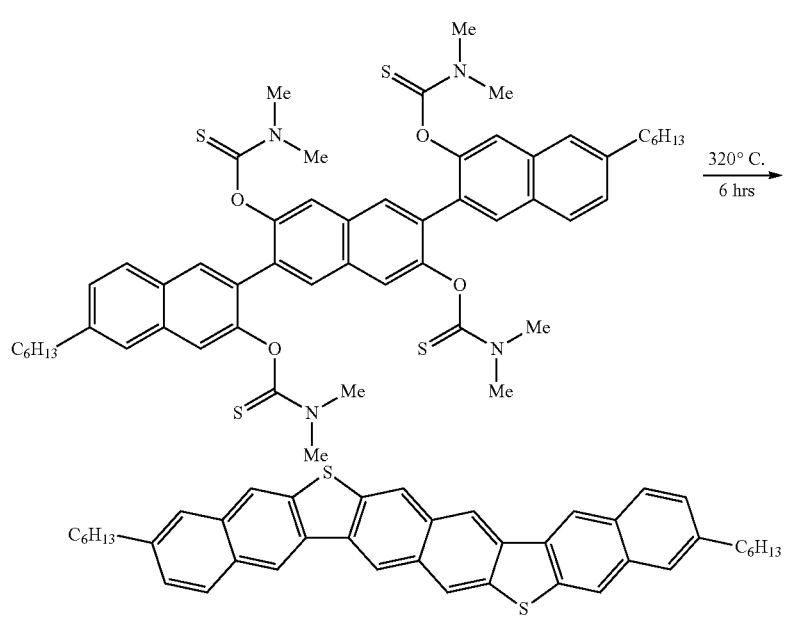

2.40 mg (2.50 mmol) of O,O',O",O'"-(6,6"-dihexyl-[2,2':6',2"-ternaphthalene]-3,3',3",7'-tetrayl)tetrakis(dimethylcarbamothioate) was sealed in a Pyrex (registered trademark) tube, and heated at 320° C. for 6 hours. The temperature was put back at room temperature, the tube was unsealed, the resulted inside material was put into ultrasonic cleaning process in chloroform, and then filtered and thermally recrystallized in 1,1,2,2-tetrachloroethane to obtain the titled compound in yellow solid (792 mg, 1.30 mmol). The yield was 52%. The physical property values of the obtained compound are shown as follows.

Melting point: 300° C. or more. $^1$H NMR (600 MHz, CDCl$_2$CDCl$_2$, 100° C.): δ0.85 (t, J=7.2 Hz, 6H, CH$_3$), 1.26-1.45 (m, 12H, (CH$_2$)$_3$), 1.71 (quin, J=7.2 Hz, 4H, ArCH$_2$CH$_2$), 2.77 (t, J=7.2 Hz, 4H, ArCH$_2$), 7.36 (d, J=8.4 Hz, 2H, ArH), 7.63 (s, 2H, ArH), 7.95 (d, J=8.4 Hz, 2H, ArH), 8.13 (s, 2H, ArH), 8.37 (s, 2H, ArH), 8.65 (s, 2H, ArH), 8.69 (s, 2H, ArH). TOF HRMS (APCI+): Calcd for C42H41S2 [M+H] 609.2650, found, 609.2643. Anal. Calcd for C42H40S2: C, 82.85; H, 6.62. Found: C, 82.71; H, 6.71.

Example 9

Synthesis of dinaphtho[2,3-d:2',3'-d']naphtho[1,2-b:6,7-b']dithiophene

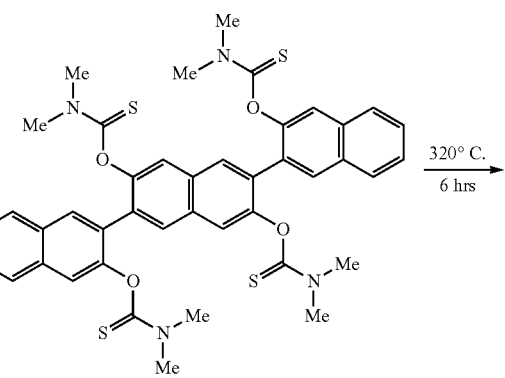

-continued

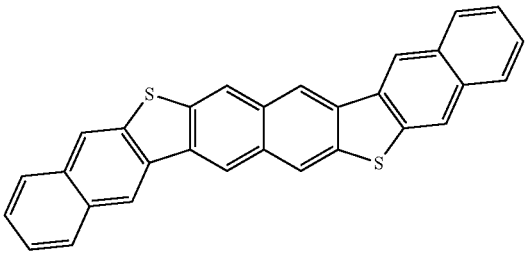

The titled compound in yellow solid (220 mg, 0.50 mmol) was obtained in accordance with the fourth step of Example 8, except that the starting raw material was changed to 793 mg (1.00 mmol) of O,O',O",O'''-([2,2':6',2"-ternaphthalene]-3,3',3",7'-tetrayl)tetrakis(dimethylcarbamothioate). The yield was 50%. The physical property values of the obtained compound are shown as follows.

Melting point: not observed, $^1$H NMR (400 MHz, CDCl$_2$CDCl$_2$, 140° C.): δ 7.53-7.58 (m, 4H, ArH), 7.90 (d, J=7.6 Hz, 2H, ArH), 8.07 (d, J=7.6 Hz, 2H, ArH), 8.22 (s, 2H, ArH), 8.73 (s, 2H, ArH), 8.75 (s, 2H, ArH).

Example 10

Synthesis of 3,11-didodecyldinaphtho[2,3-d:2',3'-d'] benzo[1,2-b:4,5-b']dithiophene

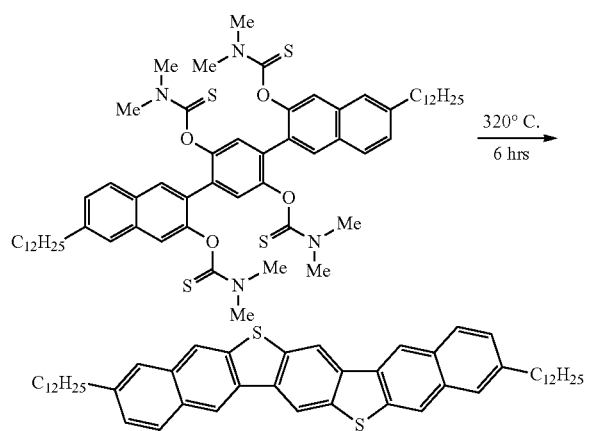

The titled compound in yellow solid (364 mg, 0.50 mmol) was obtained in accordance with the second step of Example 2, except that the starting raw material was changed to O,O'-(2,5-bis(6-dodecyl-3-((dimethylcarbamoylthioyl)oxy) naphthalene-2-yl)-1,4-phenylene)bis(dimethylcarbamothioate) (1.09 g, 1.00 mmol). The yield was 50%. The physical property values of the obtained compound are shown as follows.

Melting point: 300° C. or more. $^1$H NMR (400 MHz, CDCl$_2$CDCl$_2$, 100° C.): δ 0.88 (t, J=6.8 Hz, 6H, CH$_3$), 1.26-1.45 (m, 36H, (CH$_2$)$_3$), 1.77 (quin, J=7.2 Hz, 4H, ArCH$_2$CH$_2$), 2.83 (t, J=7.2 Hz, 4H, ArCH$_2$), 7.38 (d, J=8.4 Hz, 2H, ArH), 7.67 (s, 2H, ArH), 7.95 (d, J=8.4 Hz, 2H, ArH), 8.20 (s, 2H, ArH), 8.61 (s, 4H, ArH).

Comparative Example 1

Synthesis of dinaphtho[2,3-d:2',3'-d']benzo[1,2-b:4, 5-b']dithiophene

The titled compound was obtained by synthesis according to Example 2 except using 2-methoxynaphthalene as a starting raw material. The physical property values of the obtained compound are shown as follows.

Melting point: No melting point was observed. $^{13}$C NMR (150 MHz, CDCl$_2$CDCl$_2$): δ41.26, 41.38, 90.74, 91.26, 109.32, 111.87, 113.19, 113.78, 114.20, 114.32, 115.39, 115.56, 115.65, 119.45, 140.27, 141.66. TOF HRMS (APCI+): Calcd for C$_{34}$H$_{29}$O$_4$ [M+H] 501.2066, found, 501.2068. Anal. Calcd for C$_{58}$H$_{78}$N$_4$O$_4$S$_4$: C, 68.06; H, 7.68; N, 5.47. Found C, 68.13; H, 7.75; N, 5.31.

[Evaluation of Thermal Stability]

A thermal analysis measurement was performed on the compound synthesized in Example 4 using TG/DTA (RIGAKU Thermo Plus EvoII TG 8120) at 5° C. per minute of the ratio of heating, and 5% weight reduction was observed at 426° C. Also the measurement was performed using DSC (RIGAKU Thermo Plus Evo DSC 8270) at 5° C. per minute of the ratio of heating, and phase transition points were observed at 217° C. and 260° C.

As the same way, the measurement was performed on the compound synthesized in Example 7. Consequently, the 5% weight reduction was observed at 450° C. Also as the result of DSC measurement, no phase transition point was observed at room temperature to 300° C. According to the above, the compound of the present invention is clearly found to have very high thermal stability.

[Evaluation of Chemical Stability]

A film having a thickness of 100 nanometers formed by performing vacuum deposition of the compound synthesized in Example 4 was allowed to stand for one week in atmospheric air. The results obtained by measuring UV-Vis spectra (device used: Jasco V-570 Spectrometer, made by JASCO Corporation) over time during the period are shown in FIG. 3. Also concerning the compound synthesized in Example 7, the results of the measurement in the same way are shown in FIG. 4. As a result, no change of the spectrum was observed even in each film allowed to stand for one week. According to the above, the compound of the present invention is clearly found to be chemically stable too.

[Preparation of Organic Transistor Device and Evaluation of Characteristics Thereof]

<Edge-Cast Method>

In accordance with an application method (edge-cast method; Appl. Phys. Exp. 2, 111501 (2009)) developed by the present inventors, film formation and preparation of a bottom gate-top contact type organic FET were performed. A conceptual diagram of the method is shown in FIG. 2.

Surface treatment was performed to a silicon substrate (made by Fujimi Fine Technology Inc.) by decyltriethoxysilane (DTS) to obtain a silicon substrate (hereinafter, also referred to as "substrate") with a thermally oxidized silicon insulating film (film thickness: 500 nm). On the substrate, a solution-holding silicon substrate fragment (hereinafter, also referred to as "solution holding structure") was placed. While inclining the substrate, an 1,2-dimethoxybenzene solution of a chalcogen-containing organic compound synthesized in Examples or a 1,2-dichloroethane solution thereof (concentration of chalcogen-containing organic compound: 0.2 mass %) (organic semiconductor solution) was dripped at 120° C. onto an edge of the solution holding structure. While a crystal grew with evaporation of the solvent, the crystal stuck to the substrate, and crystal growth was completed in several minutes. In this state, the grown crystal was allowed to stand overnight (11 hours) under argon atmosphere at 60 to 100° C. to completely dry a crystal film (film thickness: 30 to 150 nm). On the crystal film obtained, a carrier injection layer (film thickness: 1 nm) of tetrafluorotetracyanoquinodimethane was formed through a stainless-steel metallic mask, and subsequently a gold source electrode and a gold drain electrode (film thickness: 30 nm) were vapor-deposited in vacuo to form a channel length of 100 μm and a channel width of 1 mm and to prepare a bottom gate-top contact type organic FET. Carrier mobility and an ON/OFF ratio were measured on the thus prepared device using Semiconductor Parameter Analyzer (model number "Keithley 4200", made by Keithley Instruments Inc.).

Preparation of the organic transistor device and evaluation of characteristics thereof as described above were performed on the compounds obtained in Examples 2, 3 to 5. The results of the evaluation are shown in Table 1. In addition, in the compound of Comparative Example 1, preparation of a two-dimensional crystal film with high quality was not allowed according to the solution process, and film formation by the above application method was difficult. As a result, with regard to the compound in Comparative Example 1, preparation of the organic transistor device by the above application method and evaluation of the characteristics thereof were not possible.

<Comparison of FET Characteristics by Vapor Deposition Method>

Device preparation by the application method was not possible with regard to the chalcogen-containing organic compound in Comparative Example 1. Therefore, a device was prepared by the vapor deposition method for the chalcogen-containing organic compounds in Examples 1, 3, 4, 7 and Comparative Example 1, and FET characteristics were compared.

Ultrasonic cleaning was performed to a silicon substrate with the thermally oxidized silicon insulating film (film thickness: 500 nm) described above for 5 minutes using acetone and 2-propanol for each, and subsequently UV ozone treatment was performed for 30 minutes. On a surface of the substrate subjected to cleaning treatment, a self-assembled monolayer of DTS was formed according to a vapor method, and then a chalcogen-containing organic compound was vapor-deposited at a vapor deposition rate of 0.4 to 0.6 Å/s to form an organic semiconductor layer having a film thickness of 75 nm. Subsequently, a carrier injection layer (film thickness: 1 nm) of tetrafluorotetracyanoquinodimethane was formed through a stainless-steel metallic mask, and subsequently a gold source electrode and a gold drain electrode (film thickness: 30 nm) were vapor-deposited in vacuo to form a channel length of 100 μm and a channel width of 1 mm and to prepare a bottom gate-top contact type organic FET.

Carrier mobility and an ON/OFF ratio were measured on the thus prepared device using Semiconductor Parameter Analyzer (model number "Keithley 4200", made by Keithley Instruments Inc.).

As a result, when the organic semiconductor material of Example 4 was used for formation of the organic semiconductor layer, carrier mobility was 1.4 $cm^2/V \cdot s$ and the ON/OFF ratio was $10^4$. On the other hand, when the organic semiconductor material in Comparative Example 1 was used for formation of the organic semiconductor layer, carrier mobility was 0.08 $cm^2/V \cdot s$ and the ON/OFF ratio was $10^4$. The results including other results are shown in Table 1.

TABLE 1

| Organic semiconductor material | Carrier mobility ($cm^2/V \cdot s$) | ON-OFF ratio | Film-forming method |
|---|---|---|---|
| Example 1 (structure with O, $C_{10}H_{21}$ groups) | 0.78 | $10^5$ | Vapor deposition |
| Example 2 (structure with S, $C_{10}H_{21}$ groups) | 0.015 | $10^5$ | Edge-cast |
| Example 3 (structure with O, $C_{10}H_{21}$ groups) | 0.24 | $10^5$ | Vapor deposition |
| | 0.50 | $10^5$ | Edge-cast |
| Example 4 (structure with S, $C_{10}H_{21}$ groups) | 16 | $10^7$ | Edge-cast |
| | 1.4 | $10^4$ | Vapor deposition |

TABLE 1-continued

| | Organic semiconductor material | Carrier mobility (cm²/V·s) | ON-OFF ratio | Film-forming method |
|---|---|---|---|---|
| Example 5 | 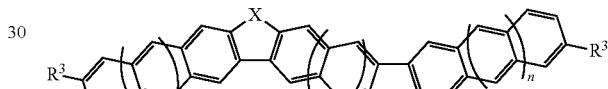 | 1.3 | $10^6$ | Edge-cast |
| Example 7 | | 0.90 | $10^5$ | Vapor deposition |
| Comparative Example 1 | | 0.08 | $10^4$ | Vapor deposition |

Characteristics of a sample of the compound of Example 4 as formed into a film with the edge-cast method were evaluated. The transfer characteristics in linier zone are shown in FIG. 5, the transfer characteristics in saturating zone are shown in FIG. 6, and the output characteristics are shown in FIG. 7.

According to the above results, it is found that the organic semiconductor materials synthesized in each Example have; (1) more excellent solubility in a solvent, (2) substantially higher carrier mobility not depending on film formation methods; than the organic semiconductor material synthesized in Comparative Example.

REFERENCE SIGNS LIST

10 Source electrode
20 Drain electrode
30 Gate electrode
40 Organic semiconductor layer
50 Gate insulating film
60 Substrate
70 Carrier injection layer
80 Crystal film
90 Organic semiconductor solution
100 Solution holding structure
110 Spacer
120 Solution holding plate

What is claimed is:

1. A compound represented by Formula (1-1) or Formula (1-2):

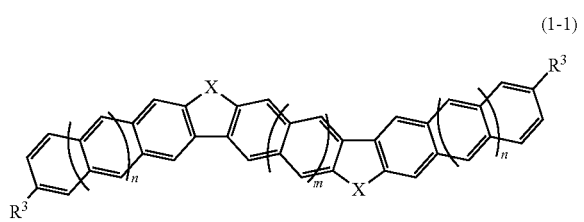

wherein, in Formula (1-1) and Formula (1-2), each X is independently sulfur, or selenium; m is 0 or 1; each n existing at two positions is 0; and each $R^3$ existing at two positions is independently fluorine, alkyl having 1 to 20 carbons, aryl, pyridyl, furyl, thienyl or thiazolyl, wherein at least one hydrogen in the alkyl may be replaced with fluorine, and at least one hydrogen on a ring of the aryl, pyridyl, furyl, thienyl and thiazolyl may be replaced with at least one selected from the group consisting of fluorine and alkyl having 1 to 10 carbons.

2. The compound described in claim 1, wherein $R^3$s in Formula (1-1) and Formula (1-2) are the same group selected from the group consisting of alkyl having 1 to 20 carbons, phenyl, furyl and thienyl.

3. The compound described in claim 2, wherein $R^3$s in Formula (1-1) and Formula (1-2) are the same group selected from the group consisting of alkyl having 6 to 12 carbons.

4. The compound described in claim 1, wherein in Formula (1-1) and Formula (1-2), each $R^3$ is independently alkyl having 1 to 20 carbons or aryl, wherein at least one hydrogen in the alkyl may be replaced with fluorine, and at least one hydrogen on a ring of the aryl may be replaced with at least one selected from the group consisting of fluorine and alkyl having 1 to 10 carbons.

5. A method for producing a compound represented by Formula (1):

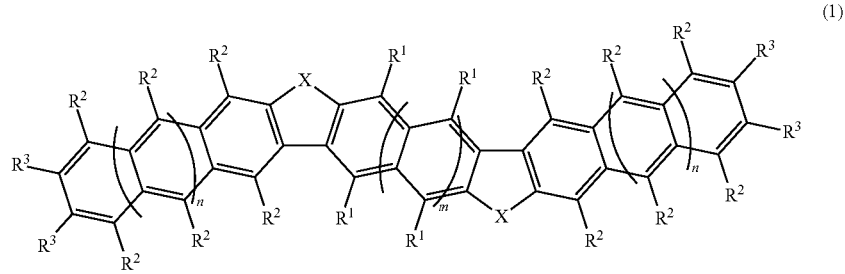

wherein, in Formula (1), each X is independently sulfur, or selenium; m is 0 or 1; each n existing at two positions is independently 0 or 1; R¹-R³ are each independently hydrogen, fluorine, alkyl having 1 to 20 carbons, aryl, pyridyl, furyl, thienyl or thiazolyl, wherein at least one hydrogen in the alkyl may be replaced with fluorine, and at least one hydrogen on a ring of the aryl, pyridyl, furyl, thienyl and thiazolyl may be replaced with at least one selected from the group consisting of fluorine and alkyl having 1 to 10 carbons;
wherein
(i) in the case of m=0, it is excluded that all of R¹-R³ are hydrogen at the same time;
(ii) in the case that m is 0 and both of n are 0, and in the case that m is 0, one of n is 0 and the other is 1, it is excluded that both of X are sulfur and all R³s are the same atoms or groups at the same time;
(iii) in the case that m is 0 and both of n are 1, it is excluded that all R³s are the same atoms or groups at the same time, and at least one of R³s is hydrogen,
wherein the method comprises:
a step of cross-coupling a compound represented by Formula (11) and a compound represented by Formula (12) to obtain a compound represented by Formula (13);
a step of deprotecting a methoxy from the compound represented by Formula (13) to obtain a compound represented by Formula (14);
a step of allowing the compound represented by Formula (14) to react with N,N-dialkyl carbamoylthiochloride or N,N-dialkyl carbamoylselenochloride to obtain a compound represented by Formula (15); and
a step of heating the compound represented by Formula (15) to obtain the compound represented by Formula (1),

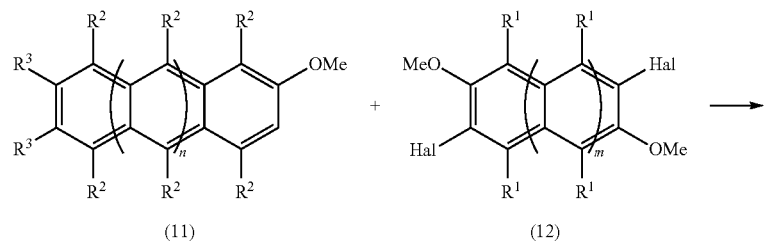

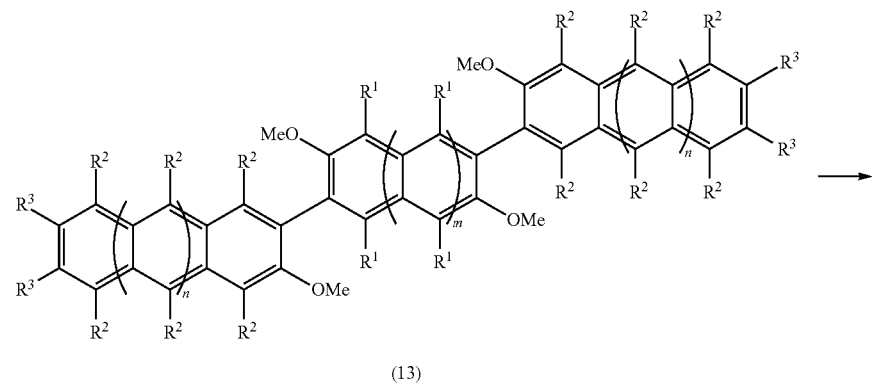

-continued

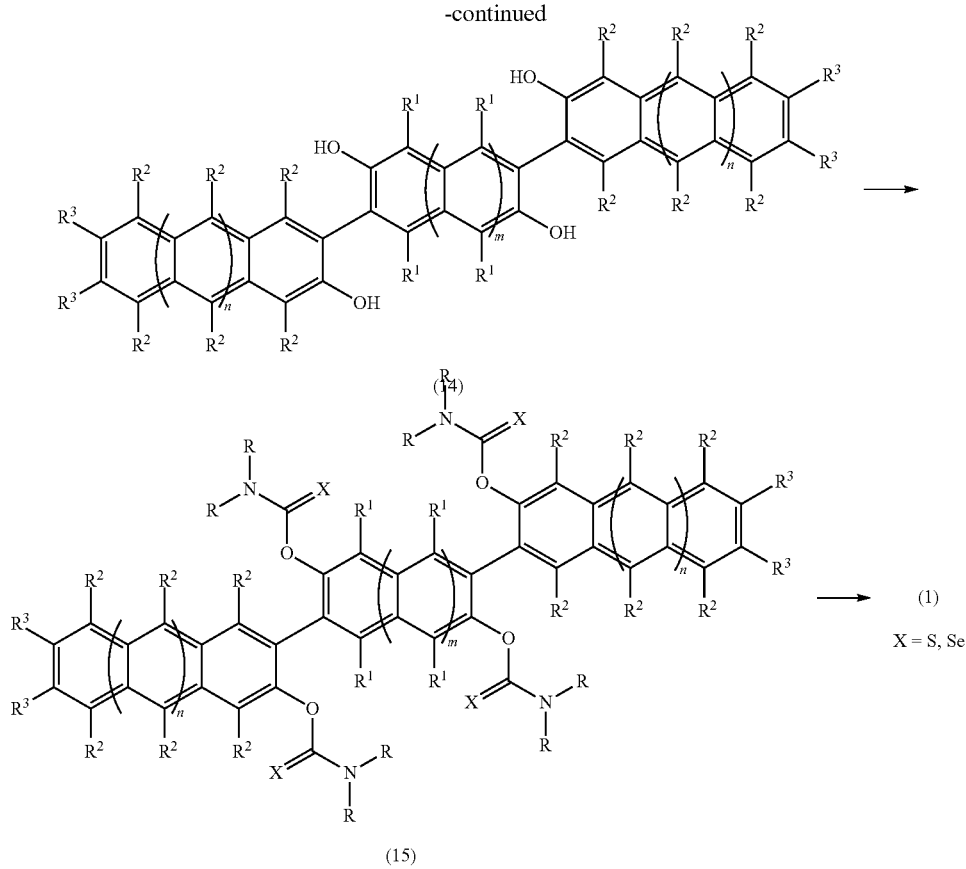

wherein, in Formulae (11)-(15), the definitions of m, n and R¹-R³ are the same as the corresponding symbols in Formula (1) respectively, Me is methyl, Hal is bromine or iodine, and each R is independently alkyl having 1-3 carbons.

6. A method for producing a compound represented by Formula (1):

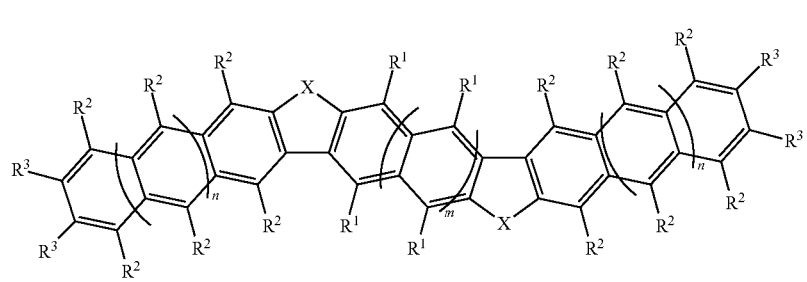

wherein, in Formula (1), each X is oxygen; m is 0 or 1; each n existing at two positions is independently 0 or 1; R¹-R³ are each independently hydrogen, fluorine, alkyl having 1 to 20 carbons, aryl, pyridyl, furyl, thienyl or thiazolyl, wherein at least one hydrogen in the alkyl may be replaced with fluorine, and at least one hydrogen on a ring of the aryl, pyridyl, furyl, thienyl and thiazolyl may be replaced with at least one selected from the group consisting of fluorine and alkyl having 1 to 10 carbons;

wherein (i) in the case of m=0, it is excluded that all of R¹-R³ are hydrogen at the same time;

(ii) in the case that m is 0 and both of n are 1, it is excluded that all R³s are the same atoms or groups at the same time, and at least one of R³s is hydrogen, wherein the method comprises:

a step of cross-coupling a compound represented by Formula (11) and a compound represented by Formula (12) to obtain a compound represented by Formula (13);

a step of deprotecting a methoxy from the compound represented by Formula (13) to obtain a compound represented by Formula (14); and a step of heating and dehydrating the compound represented by Formula (14) under a zeolite catalyst to obtain the compound represented by Formula (1),

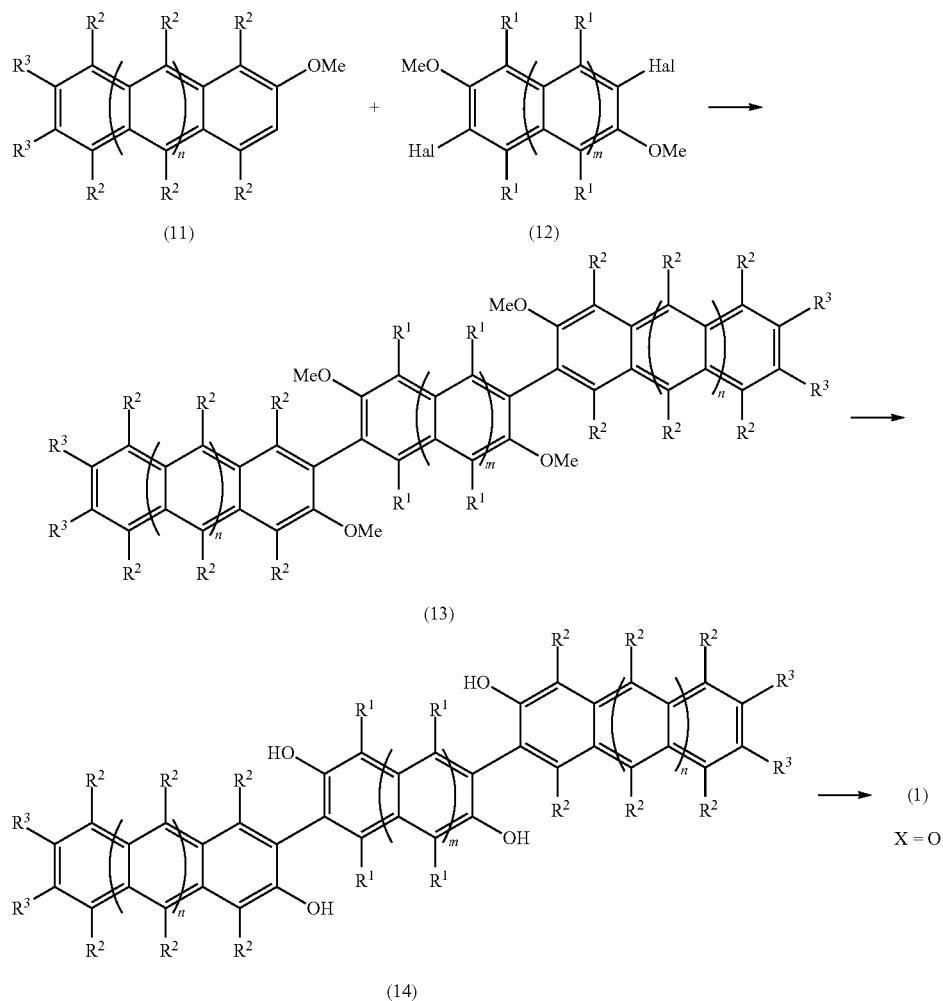

wherein, in Formulae (11)-(14), the definitions of m, n and $R^1$-$R^3$ are the same as the corresponding symbols in Formula (1) respectively, Me is methyl, and Hal is bromine or iodine.

7. An organic semiconductor material comprising the compound described in claim 1.

8. An organic semiconductor film comprising the organic semiconductor material described in claim 7.

9. An organic field effect transistor comprising a substrate, a gate electrode, a gate insulating film, a source electrode, a drain electrode and an organic semiconductor layer, wherein the organic semiconductor layer is constituted of the organic semiconductor film described in claim 8.

* * * * *